(12) United States Patent
Zhu et al.

(10) Patent No.: US 10,939,847 B2
(45) Date of Patent: Mar. 9, 2021

(54) RADIO FREQUENCY AND OPTICAL READER SCANNING ARRAY

(71) Applicant: Verily Life Sciences LLC, Mountain View, CA (US)

(72) Inventors: Jiang Zhu, Cupertino, CA (US); Stephen O'Driscoll, San Francisco, CA (US); Sean Korhummel, San Carlos, CA (US); Travis Deyle, San Jose, CA (US); Peng Cong, Cupertino, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 288 days.

(21) Appl. No.: 14/877,347

(22) Filed: Oct. 7, 2015

(65) Prior Publication Data

US 2017/0100056 A1   Apr. 13, 2017

(51) Int. Cl.
*A61B 5/07* (2006.01)
*G06K 7/10* (2006.01)
(Continued)

(52) U.S. Cl.
CPC .............. *A61B 5/07* (2013.01); *A61B 5/0015* (2013.01); *A61B 5/0017* (2013.01);
(Continued)

(58) Field of Classification Search
None
See application file for complete search history.

(56) References Cited

U.S. PATENT DOCUMENTS 5,935,078 A    8/1999  Feierbach
8,010,205 B2*  8/2011  Rahman ............... A61N 1/3787
                                                  607/60

(Continued)

FOREIGN PATENT DOCUMENTS

JP    2010-46181 A    3/2010
JP    2012-60626 A    3/2012
(Continued)

OTHER PUBLICATIONS

Chua et al.—High-Q RF coils on silicon integrated circuits; MEMS Components and Applications for Industry, Automobiles, Aerospace, and Communication II, Proceedings of SPIE vol. 4981 (2003).*

(Continued)

*Primary Examiner* — Kaylee R Wilson
*Assistant Examiner* — Jay B Shah
(74) *Attorney, Agent, or Firm* — McDonnell Boehnen Hulbert & Berghoff LLP

(57) ABSTRACT

A reader device includes an array of antenna coils configured to electromagnetically couple with devices implanted beneath or within skin of a human body. An implanted device can include a loop antenna or other means configured to couple with at least one antenna coil of the reader device to receive radio frequency energy from and transmit radio frequency transmissions to the reader device. The antenna coil array is configured to mount to the skin surface to improve the coupling between the implanted device and coils of the array. Further, the reader device is configured to select one or more antenna coils of the array and to operate the selected antenna coil to communicate, via radio frequency transmissions, with and/or provide radio frequency power to the implanted device. An antenna coil of the array can be selected based on a detected amount of coupling with the implanted device.

19 Claims, 6 Drawing Sheets

(51) Int. Cl.
  *H01Q 1/22* (2006.01)
  *H04B 1/034* (2006.01)
  *A61B 5/00* (2006.01)
  *H02J 50/10* (2016.01)
  *A61B 5/02* (2006.01)
  *H02J 50/80* (2016.01)

(52) U.S. Cl.
  CPC .............. *A61B 5/0031* (2013.01); *A61B 5/02* (2013.01); *G06K 7/10158* (2013.01); *G06K 7/10336* (2013.01); *G06K 7/10356* (2013.01); *H01Q 1/2216* (2013.01); *H02J 50/10* (2016.02); *H02J 50/80* (2016.02); *H04B 1/0343* (2013.01); *A61B 2560/0219* (2013.01)

(56) References Cited

U.S. PATENT DOCUMENTS

| | | | |
|---|---|---|---|
| 9,055,917 | B2 | 6/2015 | Mann et al. |
| 2004/0046698 | A1* | 3/2004 | Martin ............... G06K 7/10336 343/700 MS |
| 2005/0110674 | A1* | 5/2005 | Mendolia ................. G01S 5/04 342/81 |
| 2008/0042558 | A1* | 2/2008 | Buchhauser ........ H01L 27/3225 313/504 |
| 2008/0096495 | A1 | 4/2008 | Shen |
| 2010/0280568 | A1 | 11/2010 | Bulkes et al. |
| 2010/0298687 | A1 | 11/2010 | Yoo et al. |
| 2010/0298720 | A1 | 11/2010 | Potkay |
| 2012/0038443 | A1 | 2/2012 | Kubo et al. |
| 2013/0041235 | A1 | 2/2013 | Rogers et al. |
| 2014/0371824 | A1 | 12/2014 | Mashiach et al. |
| 2015/0025613 | A1 | 1/2015 | Nyberg et al. |
| 2015/0065837 | A1 | 3/2015 | Abreu |
| 2015/0080982 | A1 | 3/2015 | Van Funderburk |
| 2015/0231402 | A1* | 8/2015 | Aghassian ......... A61N 1/37229 607/59 |

FOREIGN PATENT DOCUMENTS

JP  2014-131199 A  7/2014
WO  2015/092747  6/2015

OTHER PUBLICATIONS

Zou You et al., "Implant Position Estimation Via Wireless Power Link", IEEE Transactions on Circuits and Systems II, vol. 62, No. 2, Feb. 1, 2015, pp. 139-143.

Zongxia Mou et al., "An Analytical Model for Inductively Coupled Multichannel Implantable System With Micro-Coil Array", IEEE Transactions on Magnetics, vol. 48, No. 9, Sep. 1, 2012, pp. 2421-2429.

Hans De Clercq et al., "Contactless energy transfer at the bedside featuring an online power optimization strategy", Sensors and Actuators A: Physical, vol. 217, Sep. 1, 2014, pp. 160-167.

International Searching Authority, International Search Report and Written Opinion for PCT/US2016/050637 dated Nov. 7, 2016.

* cited by examiner

RADIO FREQUENCY AND OPTICAL READER SCANNING ARRAY

BACKGROUND

Unless otherwise indicated herein, the materials described in this section are not prior art to the claims in this application and are not admitted to be prior art by inclusion in this section.

Certain medical conditions or states can be characterized by values and/or changes over time of a physiological property (e.g., a flow rate and/or amount of blood in a portion of vasculature, an oxygen saturation of blood, a blood pressure). Such physiological properties can be measured by a device located outside the body. Additionally or alternatively, an implanted or wearable device could be employed to provide continuous or near-continuous measurement of such physiological properties. Such implantable or wearable devices can be battery powered and/or powered by radio frequency energy or other wireless energy sources. Further, such devices can be configured to indicate measured physiological properties wirelessly (e.g., by using an RFID antenna and transmitter, by using a Bluetooth antenna and transmitter).

SUMMARY

Some embodiments of the present disclosure provide a device including: (i) an array of antenna coils that is configured to be mounted proximate a skin surface and to span a specified area of the skin surface, such that each antenna coil of the array of antenna coils has a respective degree of electromagnetic coupling with an antenna of an implanted device that is implanted beneath the skin surface; (ii) a controller that is operably coupled to the array of antenna coils and that includes a computing device programmed to perform controller operations. The controller operations include: (a) selecting an antenna coil of the array of antenna coils; and (b) operating the selected antenna coil, wherein operating the selected antenna coil includes at least one of (1) providing wireless power to the implanted device or (2) receiving a wireless transmission from the implanted device.

Some embodiments of the present disclosure provide a device including: (i) an array of antenna coils that is configured to be mounted proximate a skin surface and to span a specified area of the skin surface, such that each antenna coil of the array of antenna coils has a respective degree of electromagnetic coupling with an antenna of an implanted device that is implanted beneath the skin surface; (ii) controller means that are operably coupled to the array of antenna coils and that include computing means programmed to perform controller operations. The controller operations include: (a) selecting an antenna coil of the array of antenna coils; and (b) operating the selected antenna coil, wherein operating the selected antenna coil includes at least one of (1) providing wireless power to the implanted device or (2) receiving a wireless transmission from the implanted device.

Some embodiments of the present disclosure provide a method including: (i) mounting a reader device to a skin surface, wherein the reader device comprises an array of antenna coils that spans a specified area of the skin surface, wherein an implanted device is implanted beneath the skin surface, and wherein each antenna coil of the array of antenna coils has a respective degree of electromagnetic coupling with an antenna of the implanted device. The method further includes (ii) selecting an antenna coil of the array of antenna coils; and (iii) operating the selected antenna coil, wherein operating the selected antenna coil includes at least one of (a) providing wireless power to the implanted device or (b) receiving a wireless transmission from the implanted device.

These as well as other aspects, advantages, and alternatives, will become apparent to those of ordinary skill in the art by reading the following detailed description, with reference where appropriate to the accompanying drawings.

DETAILED DESCRIPTION

Figure 1A:
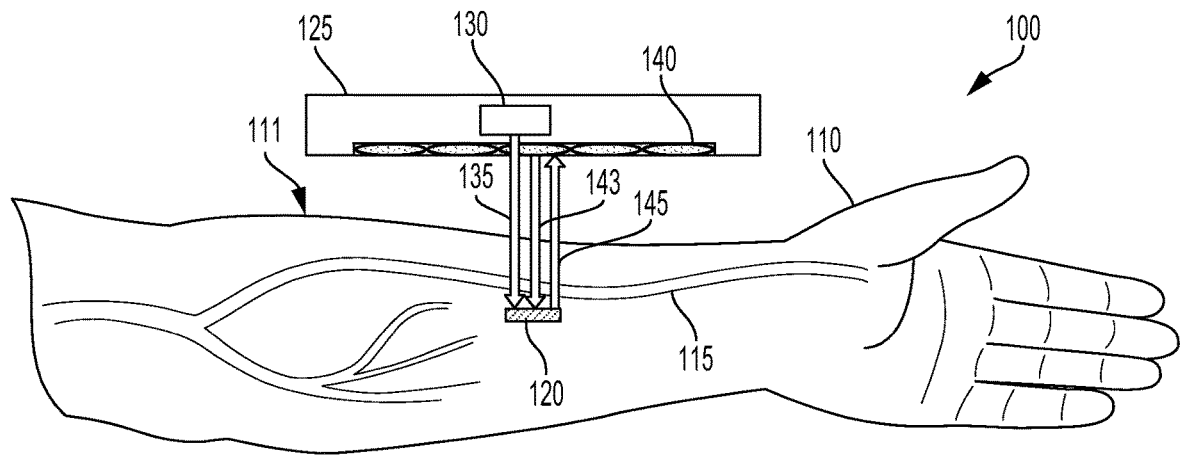
FIG. 1A is a cross-sectional view of an example reader device disposed proximate an arm and an example microelectronic device that is implanted beneath a skin surface of the arm and that is in communication with the reader device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Some embodiments of the present disclosure provide a reader device configured to be placed in contact with or otherwise mounted to a skin surface of a living body (e.g., to skin of the upper arm or abdomen of a person) and to interact with one or more devices implanted within and/or beneath the skin. Such implanted devices could each include one or more sensors configured to detect variables of the body, e.g., to detect variables related to hemodynamic properties of vasculature and/or blood in the skin. The reader device is configured to communicate with and/or provide power to the implanted devices optically, electromagnetically, or through some other means. For example, the reader device could include one or more antenna coils that are operable to electromagnetically couple with an antenna of an implanted device. Such an electromagnetically coupled antenna coil could be used to deliver radio frequency energy to the implanted device and/or to receive a wireless transmission from the implanted device (e.g., by detecting a pattern over time in an amount of radio frequency energy that is reflected and/or backscattered by the implanted device).

A degree of electromagnetic coupling between an implanted device and an antenna coil could be related to a variety of factors. Such factors can include the orientation and location of the antenna coil relative to the antenna of the implanted device. For example, a degree of coupling between an antenna coil and an antenna of an implanted device could be increased by increasing a degree of alignment between the antenna coil and the antenna of the implanted device and/or by decreasing a distance between the antenna coil and the antenna of the implanted device. The reader device can include an array of antenna coils that can be mounted proximate to a skin surface beneath which the implanted device is implanted. Each antenna coil of such an array of antenna coils could have a respective degree of electromagnetic coupling with the implanted device that is related to the respective location and/or orientation of each antenna coil relative to an antenna of the implanted device. Correspondingly, each of the antenna coils could have a respective efficiency of power transfer to the implanted device, strength of a received wireless transmission from the implanted device, or some other property of the interaction with the implanted device. In such examples, a particular antenna coil of the array of antenna coils could be selected and used to interact with the implanted device (e.g., to provide radio frequency energy to the implanted device, to receive/transmit wireless transmissions from/to the implanted device). Alternatively, more than one antenna coil could be used, e.g., as a phased array, to interact with the implanted device.

An antenna coil of an array of antenna coils could be selected according to a variety of factors using a variety of means and/or methods. The location of each of the antenna coils relative to the implanted device could be determined and used to select the nearest antenna coil to the implanted device or to select another antenna coil according to some other consideration. Determination of the relative location of the implanted device could include operating a camera or other light detecting means of the reader device, e.g., to detect an emitted and/or reflected light from the implanted device. Additionally or alternatively, the antenna coils could be operated to detect a degree of electromagnetic coupling and/or interaction between each of the antenna coils and the implanted device. For example, a signal strength of radio frequency signals received by each antenna coil (e.g., received from the implanted device) could be detected and the antenna coil having the greatest received signal strength could be determined. In some examples, such a received radio frequency signal could be transmitted by the implanted device in response to receiving radio frequency energy from the reader device. For example, each antenna coil could be operated, during a respective period of time, to emit radio frequency energy and/or to receive responsively transmitted radio frequency signals from the implanted device.

Antenna coils of an array of antenna coils as described herein could be configured in a variety of ways. The antenna coils could be substantially coplanar. The antenna coils could be non-overlapping (e.g., the array could be a hexagonal, square, triangular, or otherwise patterned regular or irregular array of tiled antenna coils) or one or more of the antenna coils could overlap. The antenna coils could have substantially the same size and/or other electromagnetic properties (e.g., impedance, resonant frequency, pattern of radio frequency emission) or could differ. The size (e.g., diameter) of the coils could be specified according to an application, e.g., based on a frequency of radio frequency energy emitted by the coils (e.g., one or more of the coils could have a diameter of approximately 3 millimeters). Further, the antenna coils could have specified shapes, e.g., hexagonal, round, elliptical, square, triangular, or other specified shapes (e.g., shapes specified to be tiled in a repeating array of overlapping or non-overlapping antenna coils).

The antenna coils of the reader device could be operated in different ways. In some examples, each antenna coil could be coupled to a respective radio frequency transmitter and/or receiver (configured, e.g., to transmit radio frequency signals and/or energy and to receive radio frequency signals, respectively). Alternatively, two or more of the antenna coils could be coupled to a single radio frequency transmitter and/or receiver, e.g., via a radio frequency switch. Such a radio frequency switch could be configured to electrically couple a selected antenna coil to an oscillator, amplifier, envelope detector, demodulator, level shifter, filter, or other components of a radio frequency transmitter and/or receiver. Further, the frequency switch could be configured to couple non-selected antenna coils to a specified high impedance or a specified low impedance such that the non-selected antenna coils do not interfere with the electromagnetic coupling between and/or interaction of the selected antenna coil and the implanted device.

The reader device could include additional elements related to the array of antenna coils and/or to the electromagnetic coupling between such coils and antennas of one or more implanted devices. In some examples, the reader device could include a conductive ground plane that is substantially parallel with the array of antenna coils and that is disposed opposite the array of antenna coils from a skin surface to which the array of antenna coils is mounted. Properties of such a ground plane (e.g., an area, a thickness, a conductivity, a distance between the ground plane and the array of antenna coils) and/or of materials interposed between the ground plane and the array of antenna coils (e.g., a low-loss spacing material or substrate layer) could be specified according to an application, e.g., to reduce interference between the array of antenna coils and other elements (e.g., electronics) of the reader device, to improve a coupling between antenna coils of the array and an implanted device, or according to some other considerations. In some examples, the reader device could include a contact layer disposed between the array of antenna coils and a skin surface to which the array of antenna coils is mounted. Such a contact layer could be configured (e.g., could have a specified thickness, composition, loss tangent, relative permittivity) to reduce interference between electrical properties of the skin surface (e.g., a conductivity, an electromagnetic loading) and the operation of the array of antenna coils, e.g., to reduce a detuning of the antenna coils related to electrical contact with and/or proximity to tissue of the skin surface.

Implanted and/or implantable devices as described herein could include a variety of sensors configured to detect a variety of physiological properties and/or properties of the environment of the implanted devices. In some examples, the sensor could include a light sensor, a pressure sensor, a strain sensor, an accelerometer, a biopotential sensor, a temperature sensor, an electrochemical sensor or some other sensor configured to detect an analyte, or some other sensor configured to detect one or more physical variables (e.g., a pressure, a displacement, a transmitted light intensity) related to hemodynamic properties of a human body, e.g., blood flow rates, blood flow velocities, pulse rates, pulse timings, blood pressures, blood oxygen saturation, pulse transit times, or other hemodynamic properties of blood, of portions of vasculature, of a heart, and/or of some other elements of the cardiovascular system of a body in which the implanted device is implanted. For example, an implanted device could be implanted proximate a portion of subsurface vasculature within skin beneath a surface of which the implanted device is located.

In some examples, the implanted device could include one or more light detectors configured to detect an intensity (or other property) of light that is transmitted from outside the skin, through the portion of subsurface vasculature, to the light detector. Such a detected intensity could be related to a volume of blood in the portion of subsurface vasculature and could be used to determine a pulse rate, blood pressure, pulse transit time, or other hemodynamic properties of the portion of subsurface vasculature and/or of blood therein. Further, the reader device could include a light emitter configured to provide such light transmitted from outside the skin surface. Additionally or alternatively, the implanted device could include a solar cell and/or could operate the light detector to receive energy from the transmitted light to power the implanted device.

The reader device could include an array of light emitters, each configured to provide optical wireless power to the implanted device, to transmit optical wireless transmissions (e.g., coded patterns and/or pulses of emitted light) to the implanted device, to provide illumination to a light sensor of the implanted device (e.g., to allow detection of a property of a portion of subsurface vasculature through which the illumination passes), or to provide some other function by emitting light toward the implanted device. Each light emitter of such an array could be associated with one or more of the antenna coils of the antenna array of the device, and light emitters could be operated based on such associations. For example, one or more light emitters associated with a selected antenna coil (that is, an antenna coil that has been selected to be operated to provide wireless power to, to receive wireless transmissions from, or otherwise interact with an implanted device) could be operated to provide illumination to power the implanted device, to provide illumination to a sensor of the implanted device, or to provide some other function. Each light emitter of the array of light emitters could be associated with a single corresponding antenna coil of the array of antenna coils (e.g., each light emitter could be located at the center of a corresponding antenna coil); alternatively, each light emitter could be associated with a number of antenna coils and/or each antenna coil could be associated with a number of light emitters.

Those of skill in the art will recognize that reader devices, implanted/implantable devices, and other devices, systems, and methods described herein may be provided in devices that could be mounted on, proximate to, and/or within a variety of portions of the human body to measure a variety of physiological and/or hemodynamic properties of the human body (e.g., concentrations of a variety of analytes in a variety of fluids of the body, temperature, galvanic properties, ECG, muscle activity, blood flow rate, blood flow velocity, blood pressure, blood oxygenation, pulse transit time). Those of skill in the art will also recognize that the implantable devices described herein may be provided in devices that could be implanted or otherwise located in locations other than locations within skin of a human body, e.g., locations in some other tissue of a human body, locations in an animal body, locations that are part of a natural or artificial environment. Correspondingly, reader devices described herein could be configured to be mounted on and/or proximate to the locations of such implanted devices and to electromagnetically power, communicate with, or otherwise interact with such implanted devices.

It should be understood that the above embodiments, and other embodiments described herein, are provided for explanatory purposes, and are not intended to be limiting.

II. EXAMPLE READER DEVICE

In a variety of applications, it can be beneficial to place a sensor in an environment of interest, e.g., to implant an implantable sensing platform within tissue of a person to detect physiological and/or hemodynamic parameters of the person. Placing a sensor in an environment of interest can allow for detection of a property of interest, e.g., improved detection of a pulse rate, a blood flow rate, an optical or other property of blood or other tissue, a concentration of an analyte in a fluid, or some other parameters of a person, e.g., of a portion of subsurface vasculature and/or of blood therein. For example, a sensor configured to detect one or more hemodynamic parameters and/or physical variables related thereto could be placed proximate a portion of subsurface vasculature. Such improved detection could be related to a reduced distance between a sensor and a target of interest, a reduced amount of tissue or other material intervening between a sensor and a target of interest, an increased stability of the interface between a sensor and the environment of a target of interest (e.g., a reduction of relative motion between the sensor and the target due to emplacement of the sensor proximate the target within an environment that also contains the target), or other factors.

Such a sensor implanted within a human body (e.g., beneath a skin surface, proximate a portion of subsurface vasculature) could be configured in a variety of ways. In some examples, a sensor could be part of an implanted device that is configured to wirelessly communicate with (e.g., to transmit sensor readings), receive energy from, or otherwise interact with other devices (e.g., reader devices configured to communicate with, provide energy to, or otherwise interact with the implanted device) through a skin surface beneath which the implanted device is implanted. Such interaction could include the transmission and/or reception of optical energy, radio frequency energy, or other energies or fields that are able to be transmitted through intervening tissue (e.g., through the skin surface). For example, the implanted device could include an antenna (e.g., a loop of wire or coil) configured to electromagnetically couple with one or more corresponding antenna coils of a reader device.

Such electromagnetic coupling can allow electromagnetic fields generated by one of the reader device or the implanted device (e.g., by driving the antenna coil or antenna, respectively, with a time-varying voltage and/or current) to be received by the opposite device. For example, the reader device could operate the antenna coil to provide wireless power to the implanted device, to transmit a wireless transmission to the implanted device, to receive a wireless transmission from the implanted device, or to otherwise interact with the implanted device. Conversely, the implanted device could operate the antenna to transmit a wireless transmission to the reader device (e.g., by backscattering, reflecting, or otherwise modifying radio frequency energy or fields provided by the reader device), to receive a wireless transmission from the reader device, or to otherwise interact with the reader device.

As an illustrative example, FIG. 1A shows, in cross-section, an arm 110 containing a portion of subsurface vasculature 115 located beneath a skin surface 111. An implanted device 120 is implanted beneath the skin surface 111 (e.g., at a depth beneath the skin surface 111 between approximately 1 millimeter and approximately 5 millimeters) such that the portion of subsurface vasculature 115 is positioned between the microelectronic device 120 and the skin surface 111. The portion of subsurface vasculature 115 could be an artery, a vein, a capillary, or some other portion of vasculature beneath the skin surface 111. The portion of subsurface vasculature 115 could be part of a capillary bed within the skin. A reader device 125 is located outside the skin surface 111 proximate the arm 110. The reader device 125 includes an array of antenna coils 140 that are each configured to have a degree of electromagnetic coupling with an antenna (not shown) of the implanted device 125. Such electromagnetic coupling can be related to the location and/or orientation of each of the antenna coils of the array 140 relative to the antenna of the implanted device 120, the composition or geometry of tissues of the arm proximate the devices 120, 125, or other factors. The reader device 125 further includes a light emitter 130.

Note that the illustration of an implanted device that is implanted proximate to a portion of subsurface vasculature is intended as a non-limiting example. Implanted devices as described herein could be located proximate to a variety of different elements of a body (e.g., nerves, tendons, muscle fibers, bones, organs) to detect properties of such different elements of the body. In some examples, an implanted device could be implanted proximate a tendon and could detect motion of the tendon. This could include detecting a change in a pattern of constructive and destructive interference in light received form the tendon, e.g., light scattered by, reflected by, or otherwise emitted from the tendon in response to illumination (e.g., illumination by coherent light from outside a skin surface proximate the tendon). In some examples, an implanted device could be implanted proximate a nerve or muscle fiber and could detect electrical activity (e.g., action potentials) of the nerve or muscle fiber. This could include detecting electrical fields or currents produced by the nerve or muscle fiber, e.g., by detecting a biopotential between two or more electrodes of the microelectronic device. Implanted devices as described herein could be disposed within or proximate to other tissues and configured to detect other physiological parameters and/or physical variables, or could be disposed within environments that are not part of a human body.

Further, while the reader device 125 of FIG. 1A is illustrated as being located away from the surface of the arm 111, a reader device as described herein could be configured to be placed in contact with a skin surface beneath which an implanted device is located, or in contact with the surface of some other environment or material containing a wireless sensor device as described herein.

The implanted device 120 can be configured to detect physiological and/or hemodynamic parameters of the arm 110 (e.g., a hemodynamic parameter of the portion of subsurface vasculature 115 and/or of blood therein), to detect some other properties, or to provide some other functions. Related to such operations of the implanted device 120, the reader device 125 is configured to provide (using one of the antenna coils of the array of antenna coils 140) wireless power 143 to the implanted device 120 and to receive wireless transmissions 145 from the implanted device 120. The implanted device 120 can use such provided energy to e.g., to operate a sensor to detect a physiological parameter (e.g., a hemodynamic parameter of the portion of subsurface vasculature 115), to provide the wireless transmission 145 related to such detected parameters or other information to the reader device 125, or to perform some other operations. The reader device 125 could be configured to operate the array of antenna coils 140 to provide some further functions, e.g., to transmit wireless transmissions to the implanted device 120 (e.g., by modulating a frequency, phase, amplitude, or other properties of the provided wireless power 143), to detect the location and/or orientation of the implanted device 120 relative to the reader device 125, or to provide some other functions.

The provided wireless power 143 could be radio frequency energy (e.g., electromagnetic radiation having a wavelength greater than or equal to microwave wavelengths) emitted by an antenna coil of the array of antenna coils 140. The implanted device 120 could include one or more antennas, coils, waveguides, ferrites, striplines, or other components configured to receive such radio frequency energy (e.g., to receive radio frequency energy at a specified frequency). Such energy-receiving elements could be configured to provide further functions, e.g., to receive wireless transmissions from the reader device 125 (e.g., by detecting time-varying patterns in amplitude, phase, frequency, or other properties of the received radio frequency energy), to detect a time-varying magnetic field (e.g., variations in the detected direction and/or magnitude of the Earth's magnetic field as the implanted device 120 is translated and/or rotated with motions of the arm 110), to provide radio-frequency wireless transmissions 145 to the reader device 125, or to provide some other functions according to an application.

The implanted device 120 could additionally or alternatively be powered by some other element(s) and/or sources of energy. For example, the microelectronic device 120 could include an electrochemical battery (e.g., a zinc-oxygen battery), a capacitor, or some other energy storage means that could be charged or otherwise configured to include a store of energy before implanting the implanted device 120 in a body (e.g., beneath skin surface 111). In some examples, the implanted device 120 could be configured to receive chemical energy from the environment of the implanted device 120, e.g., from glucose, ATP, or some other source(s) of chemical energy in blood, interstitial fluid, or some other substance that is contacting the implanted device 120. In some examples, the implanted device 120 could be configured to receive optical power, e.g., light from ambient light sources in the environment of the arm 110, optical power emitted from the reader device 125 (e.g., emitted light 135 from the light emitter 130), or from some other source.

The wireless transmission 145 includes a time-varying electromagnetic field (e.g., a radio frequency signal) emitted by the implanted device 120. An intensity, frequency, phase, direction or degree of polarization, or some other property of the emitted electromagnetic field could be controlled by the implanted device 120 in a manner related to information to be indicated, e.g., to provide an amplitude, phase, frequency, or otherwise-modulated carrier wave encoded to represent digital codes, binary values, or other information related a physical properties detected by one or more sensors of the implanted device, an operational state of the implanted device 120 (e.g., an amount of energy being received by the device 120), a cryptographic key or other user credential, or some other information. The emitted electromagnetic field could be generated by a coil, stripline, antenna, or other elements of the implanted device 120; additionally or alternatively, the emitted electromagnetic field could include electromagnetic energy received by the implanted device 120 and reflected by a coil, antenna, or some other element(s) of the implanted device 120 that has a controllable impedance or some other controllable electrical property. For example, an impedance could be selectively applied to terminals of a coil (or other antenna element(s)) to detune the coil such that the coil backscatters or otherwise reflects more or less received electromagnetic energy over time to indicate some information.

The light emitter 130 (e.g., an LED, a laser, or some other components configured to generate visible, infrared, ultraviolet, and/or some other wavelengths of optical energy) is configured to emit illumination 135 through the surface of the skin 111 to the implanted device 120. In some examples, the illumination 135 received by the implanted device 120 could be received by one or more light sensors of the implanted device 120 to detect parameters of the portion of subsurface vasculature 115, the arm 110, or other hemodynamic and/or physiological parameters of a body. For example, the illumination 135 could illuminate and be partially absorbed by the portion of subsurface vasculature 115. Additionally or alternatively, the illumination 135 could be provided to provide energy to the implanted device 120. An amount of the illumination 135 that is transmitted through the portion of subsurface vasculature 115 could be received by a light sensor and/or optical energy receiver of the implanted device 120 and used to power the device 120 and/or to detect one or more properties of the portion of subsurface vasculature 115 (e.g., a volume of blood in the portion of subsurface vasculature, an oxygen content of the blood). In some examples, an optical energy receiver and light sensor could include one or more elements in common. For example, a light sensor could include a photovoltaic cell and the optical energy receiver could be configured to use the photovoltaic cell to receive optical energy and to use the received optical energy to power the implanted device 120.

As shown, the illumination 135 is emitted through the array of antenna coils 140. This could include emitting the illumination 135 through a window formed through the array 140 (e.g., a window formed in the middle of one of the antenna coils of the array 140 through a substrate, conductive material, ground plane, or other elements of the device 125). Such a window could be formed by forming a hole through elements of the device 125 (e.g., forming a hole through a ground place, contact layer, spacing layer, or other layers or elements of the antenna array 140) and/or by wholly or partially forming a substrate, conductive material, coil, ground plane, or other elements of the array of antenna coils 140 from a material that is substantially transparent to the illumination 135. Additionally or alternatively, the light emitter 130 could be located at another location such that the illumination 135 can be emitted toward the implanted device 120. For example, the light emitter 130 could be disposed beneath the array of antenna coils 140 (that is, between the array of antenna coils 140 and the surface of the skin 111), to the side of the array of antenna coils 140 and configure to emit the illumination 135 toward the implanted device 120 from beyond the edge of the array of antenna coils 140, or at some other location. Further, in some examples, a reader device as described herein could not include such a light emitter that is configured to provide illumination to an implanted device.

As illustrated, the reader device 125 includes a single light emitter 130. However, the reader device 125 could include an array of light emitters, each configured to provide illumination (e.g., infrared light, visible light, ultraviolet light) to the implanted device 120 to, e.g., provide optical power to the implanted device 120, to provide illumination to a sensor of the implanted device 125 (e.g., to detect a property of the portion of subsurface vasculature 115 through which the illumination passes), to provide optical wireless communications to the implanted device 120, or to provide some other functionality. A particular one or more of the light emitters (e.g., one or more light emitters configured to illuminate portions of the arm 110 that contain the implanted device 120) could be operated to provide such illumination. In some examples, each antenna coil of the array of antenna coils 140 could be associated with one or more of the light emitters of an array of light emitters, and the light emitters associated with an antenna coil that has been selected to provide wireless power to the implanted device 120, to receive wireless transmissions from the implanted device 120, or to otherwise interact with the implanted device 120 could be operated to provide illumination (e.g., to provide optical power to the implanted device 120, to provide illumination to a light sensor of the implanted device 120).

In some examples, such an array of light emitters could include a single light emitter associated with each antenna coil of the array of antenna coils 140. For example, each light emitter could be located at the center of a corresponding antenna coil. Alternatively, a single light emitter could be associated with multiple antenna coils, e.g., a single light emitter could be provided at the center of a set of antenna coils (e.g., a set of three non-overlapping antenna coils) and associated with each of the antenna coils of the set such that the light emitter can be operated to provide illumination when any antenna coils of the set are selected to electromagnetically interact with the implanted device 120. In some examples, multiple light emitters could be associated with each antenna coil of an array of antenna coils.

In some examples, the implanted device 120 could be configured to operate independently to log a plurality of values of a detected physical variable and/or hemodynamic or physiological parameter (powered, e.g., by ambient energy sources, by a battery, by glucose or some other source of biochemical energy in the body, or by some other power source) and subsequently to provide wireless transmissions 145 indicating such logged information, e.g., to the reader device 125. Additionally or alternatively, the implanted device 120 could be configured to operate in response to receiving wireless energy 143 and/or illumination 135 from the reader device 125 and to wirelessly transmit, to the reader device 125, information related to detected physical variables, hemodynamic or physiological parameters, or some other information. In some examples, the operation of one or more sensors of the implanted device 120 to detect a hemodynamic or physiological property (e.g., a volume of blood in the portion of subsurface vasculature 115) could include detecting an interaction between the portion of subsurface vasculature 115 and/or arm 110 and the reader device 125, e.g., detecting an amount of absorption, by the portion of subsurface vasculature 115, of illumination 135 provided by a light emitter 130 of the reader device 125.

As illustrated in FIG. 1A, the reader device 125 is operating a particular antenna coil of the array of antenna coils 140 to interact with (i.e., to provide wireless power 143 to and to receive wireless transmissions 145 from) the implanted device 120. The reader device 125 could select and operate any of the antenna coils of the array of antenna coils 140 to perform such functions, or additional functions (e.g., to transmit wireless transmissions to the implanted device 120, to detect the depth of the implanted device 120 beneath the surface of the skin 111). Additionally or alternatively, more than one antenna coil of the array 140 could be operated (e.g., as a phased array to form a beam or other pattern of emitted electromagnetic energy) to provide wireless energy to, to provide wireless transmissions to, to receive wireless transmissions from, or to otherwise wirelessly interact with the implanted device 120. Further, multiple implanted devices could be disposed within the arm 110 (or some other environment of interest) and the reader device 125 could operate multiple antenna coils of the array 140 to interact with (e.g., to provide wireless energy to, to receive wireless transmissions from) multiple respective implanted devices.

Figure 1B:
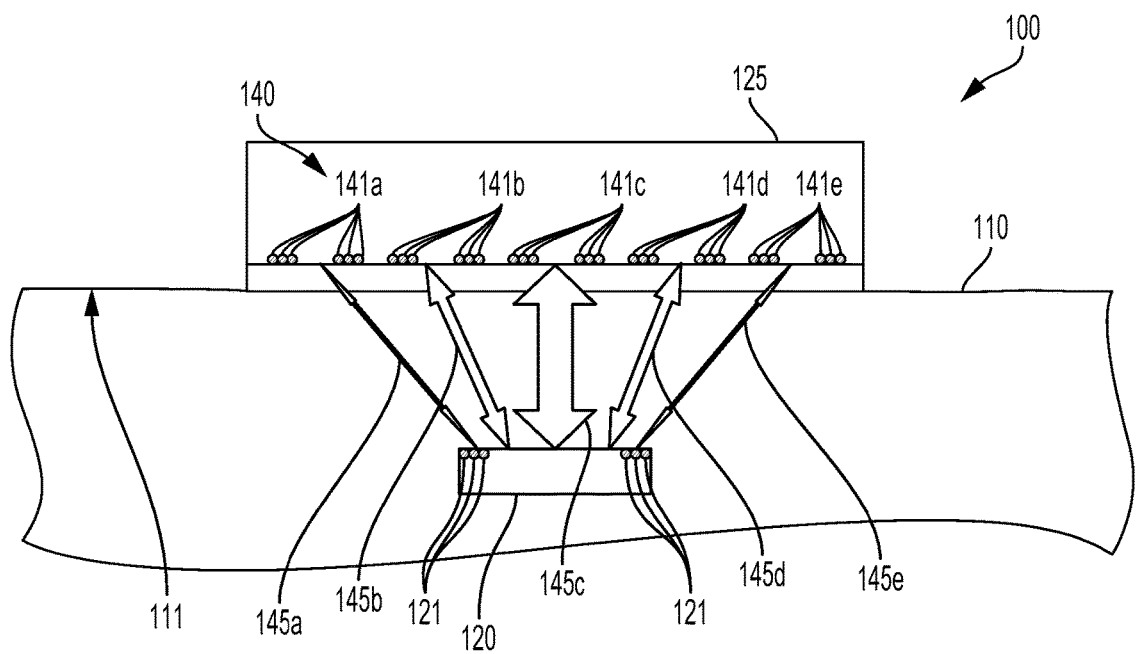
FIG. 1B is a cross-sectional view of the example reader device shown in FIG. 1A when mounted to the skin surface of the arm with illustration of the degree of electromagnetic coupling between an antenna of the implanted device and antenna coils of the reader device.

Each antenna coil of the array 140 has a respective degree of electromagnetic coupling with the antenna of the implanted device 120. To illustrate this, FIG. 1B shows the reader device 125 mounted to (e.g., held in place against by hand, strapped to, adhered to with an adhesive, or otherwise placed in contact with) the skin surface 111 of the arm 110. Five particular antenna coils 141a-e of the array of antenna coils 140 are shown in cross-section. Further, the antenna 121 of the implanted device 120 is shown in cross-section (illustrated, by way of example, as a loop antenna). The degree of electromagnetic coupling between each of the particular antenna coils 141a-e is illustrated by the thickness of respective arrows.

The degree of electromagnetic coupling between a particular antenna coil and the antenna 121 of the implanted device 120 can be related to a location or orientation of the implanted device 120 relative to the particular antenna coil, to properties of the environment of the antenna 121 and coils, or to some other factors. For example, the degree of electromagnetic coupling could decrease with increasing distance between the implanted device antenna 121. The degree of electromagnetic coupling could additionally be related to the degree of alignment (e.g., a relative angle between a characteristic axis of the implanted device antenna 121 and an antenna coil of the array 140, e.g., an axis perpendicular to the plane of an antenna coil). This is illustrated in FIG. 1B by the thickness of arrows 145a, 145e corresponding to antenna coils 141a, 141e being less thick than arrows 145b, 145d corresponding to antenna coils 141b, 141d, which are in turn less thick and the arrow 145c corresponding to the middle antenna coil 141c. The degree of coupling could additionally be related to a permittivity, permeability, conductivity, dielectric constant, or other properties of material disposed between and/or proximate to the implanted device antenna 121 and antenna coils of the array 140.

As shown, the reader device 125 is configured to mount to the skin surface 111 to minimize the distance between the implanted device antenna 121 and antenna of the array of antenna coils 140. Further, a reader device and/or an array of antenna coils thereof could be flexible, could have a curved shape, or could be configured in some other way to minimize the distance between an antenna of an implanted device and antenna coils of the array of antenna coils.

To maximize the degree of electromagnetic coupling between the implanted device antenna 121 and an antenna coil of the array 140, the array and/or the one or more antenna coils thereof could be moved to minimize a distance between the implanted device antenna 121 and the antenna coil of the array 140. This could include operating a servo or other actuator to adjust the location of the array 140 and/or elements thereof. Additionally or alternatively, a user could adjust the location of the reader device 125 on the skin, e.g., responsive to an instructing indication provided by a display or other elements of the reader device 125. Alternatively, the array 140 could include a plurality of antenna coils (as shown) that span a specified area (e.g., a specified area of the skin surface 111, when the reader device 125 is mounted thereto) and a particular antenna coil of the array (e.g., 141c) could be selected (e.g., based on a determination that the selected antenna coil has the greatest degree of electromagnetic coupling with the implanted device antenna 121). The selected antenna coil could then be operated to provide wireless energy to the implanted device 120, to receive wireless transmissions from the implanted device 120, to otherwise interact with the implanted device 120.

Figure 1C:
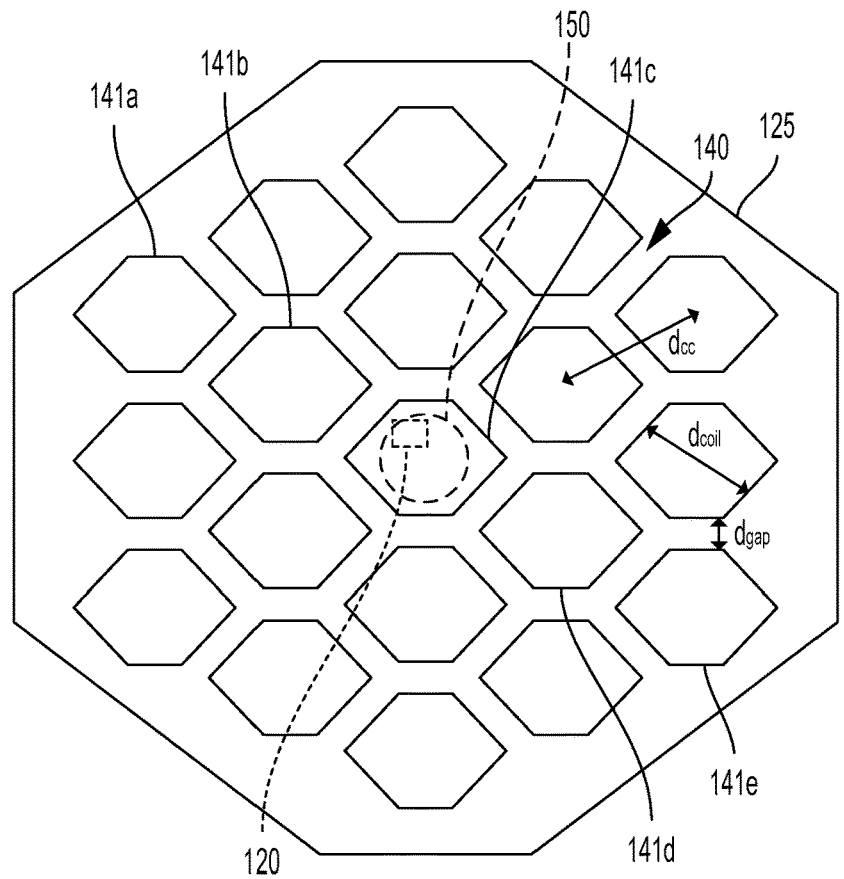
FIG. 1C is a schematic view of coils of an antenna array of the reader device shown in FIGS. 1A and 1B.

To illustrate this, FIG. 1C shows the arrangement of antenna coils (e.g., 141a-e) of the array of antenna coils 140 of the reader device. FIG. 1C also shows the location of a circular window 150 formed in the middle of one of the antenna coils 141c through which a light emitter could illuminate the implanted device 120 (e.g., to provide power to the implanted device 120, to provide illumination to a sensor of the implanted device 120, to communicate with the implanted device 120). The location of the implanted device 120 relative to the coils of the array 140 is also illustrated. Note that the sizes, shapes, and arrangements of antenna coils, the window 150, and the relative size of the implanted device 120, are intended as a non-limiting example of the configuration of an array of antenna coils that spans a specified area, e.g., a specified area of a skin surface when mounted to such a skin surface. Further, note that additional windows could be formed within other antenna coils of the array 140 (e.g., a window could be formed in the middle of each of the antenna coils of the array 140).

As shown in FIG. 1C, the antenna coils are hexagonal, have substantially the same size, are non-overlapping, and are arranged in a substantially regular, repeating pattern across the area spanned by the array 140. However, the antenna coils of an array of antenna coils of a reader device as described herein could be configured and/or arranged in some other way to span a specified array according to an application. For example, the antenna coils could be triangular, circular, square, elongate, or some other shape. Further, the antenna coils could partially overlap each other, could be arranged irregularly (that is, not in a substantially regular, repeating pattern). Further, while the illustrated array of antenna coils 140 includes antenna coils that are substantially planar and that are arranged in the array 140 such that the antenna coils are substantially coplanar, other orientations and/or arrangements of antenna coils are anticipated. For example, an array of antenna coils could include a plurality of antenna coils that have a variety of different orientations, e.g., such that an antenna coil of such an array that is most aligned with the antenna of an implanted device could be selected and used to interact with such an implanted device.

Further, a size, impedance, or other properties of the antenna coils could be specified according to an application.

For example, the antenna coils could have a size (indicated in FIG. 1C by the diameter $d_{coil}$) that is related to a frequency of radio frequency energy provided, by the antenna coils, to an implanted device. Additionally or alternatively, such a size could be specified to maximize the degree of electromagnetic coupling between the antenna coil and an implanted device that is located at a specific depth beneath the skin. In a particular example, an antenna coil could have a diameter of between approximately 3 millimeters and approximately 3.5 millimeters in order to, for example, maximize the degree of electromagnetic coupling between the antenna coil in an implanted device located between approximately 1 millimeter and approximately 2 millimeters beneath the surface of the skin. The size of the antenna coil could be increased in order to maximize the degree of electromagnetic coupling with implanted devices located at greater depths within the skin. Correspondingly, a frequency of electromagnetic energy provided by the antenna coil could be decreased. Antennas of an array of antenna coils could have respective different sizes or other respective different properties.

The distance between the antenna could be specified to minimize the degree of electromagnetic coupling between the antenna coils of the array, to maximize the area of the array that is within at least one antenna coil of the array (e.g., to minimize areas wherein the degree of electromagnetic coupling to an implanted device is low), or according to some other consideration. For example, the distance between windings of individual antenna coils of the array of antenna coils 140 (indicated in FIG. 1C by the distance $d_{gap}$) could be specified to minimize electromagnetic coupling between adjacent coils while also minimizing the area of the array 140 that is not covered by any of the antenna coils. In a particular example, distance between windings of individual antenna coils of the array of antenna coils 140, $d_{gap}$, could be approximately 0.5 millimeters. The distance between the centers of the antenna coils (indicated in FIG. 1C by the distance $d_{cc}$) could be specified based on this specified inter-antenna distance and on the size of the coils. For example, if $d_{gap}$ is approximately 0.5 millimeters and the size of the coils ($d_{coil}$) is between approximately 3 millimeters and approximately 3.5 millimeters, $d_{cc}$ could be between approximately 3.2 millimeters and approximately 3.7 millimeters. In some examples, the antenna coil having the greatest degree of electromagnetic coupling with the antenna 121 of the implanted device 120 could be determined and selected. Such a determination could include measuring the degree of coupling in some way. This could include detecting a strength of radio frequency signals received by each of the antenna coil of the array 140 and determining, based on the detected signal strengths, which antenna coil has the greatest received signal strength (e.g., 141c). In some examples, the radio frequency signal received by a particular antenna coil could be transmitted by the implanted device 120 in response to receiving wireless power from the particular antenna coil. For example, the wireless power could include radio frequency energy and the received radio frequency signal could include an amount of the wireless power that is backscattered by the antenna of the implanted device 120. In some examples, selecting an antenna coil of the array 140 could include determining the location of the implanted device 120 relative to the antenna coils of the antenna array 140 and selecting, e.g., the antenna coil that is physically closest to the implanted device 120. Other methods and/or criteria for choosing an antenna coil of an array of antenna coils to provide wireless energy to, transmit wireless transmissions to, receive wireless transmissions from, or otherwise interact with an implanted device are anticipated.

The reader device 125 could include an array of light emitters (not shown), each light emitter of the array configured to provide optical wireless energy to an implanted device, to provide optical wireless transmissions to a wireless device (e.g., programming for the implanted device, commands for the wireless device), to provide illumination to a light sensor of the implanted device (e.g., to illuminate a portion of subsurface vasculature, such that the light sensor can detect a property of light partially absorbed by, refracted by, reflected by, scattered by, or otherwise emitted from the portion of subsurface vasculature), or to provide illumination for some other purpose. Light emitters of such an array could be disposed, relative to antenna coils of the array 140, in a variety of ways. In some examples, a single light emitter could be provided for each antenna coil (e.g., disposed near the center of each antenna coil). A light emitter corresponding to a selected antenna coil could be operated to provide illumination to the implanted device 120.

In some examples, a single antenna coil could be associated with multiple light emitters and/or a single light emitter could be associated with multiple antenna coils. For example, the reader device 125 could include an array of light emitters disposed proximate the corners of each antenna coil of the array 140 (that is, a hexagonal array of light emitters, wherein the light emitters are offset from the centers of the antenna coils of the array 140). Each light emitter of the array could be associated with the antenna coils proximate the light emitter such that, e.g., when a particular antenna coil is selected, a set of six associated, neighboring light emitters can be operated to provide illumination to the implanted device 120. Other configurations of an array of light emitters relative to an array of associated antenna coils, patterns of association between such antenna coils and such light emitters, and operations of such light emitters are anticipated.

The size, shape, and composition of antenna coils of an array of antenna coils or other properties of the configuration of an antenna coil array of a reader device could be specified according to a variety of considerations. Such considerations can include maximizing a degree of electromagnetic coupling between antenna coils of the array and an antenna of an implanted device that is implanted beneath a skin surface. This can include minimizing the distance between the antenna coils and the implanted device and the reader device when the reader device is mounted to the skin surface, e.g., by configuring the reader device such that the antenna coils are in direct contact with the skin surface and/or such that the antenna coils are separated from the skin surface by a layer of protective or otherwise configured material having a specified small thickness.

Maximizing a degree of electromagnetic coupling between antenna coils of the array and the antenna of the implanted device can also include specifying a quality factor, a size, a resonant frequency, an impedance, a standing wave ratio, or some other properties of the antenna coils of the array. This can include coupling the antenna coils to respective capacitors, disposing a layer of material having a specified thickness, dielectric constant, or other properties between the antenna coils and the skin surface, e.g., to prevent detuning of the antenna coils or other effects on the electrical properties of the antenna coils by tissues of the skin. Maximizing a degree of electromagnetic coupling between antenna coils of the array and the antenna of the implanted device can include configuring the reader device according to further considerations.

Figure 2:
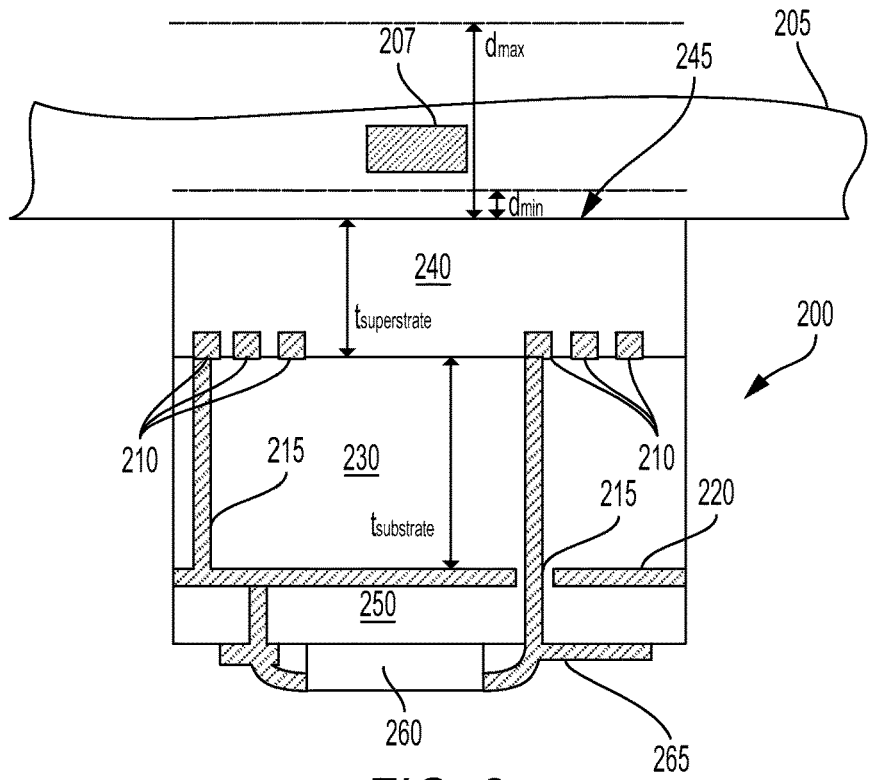
FIG. 2 is a cross-sectional schematic view of elements of an example reader device that is mounted to a skin surface of an arm and an example microelectronic device that is implanted beneath the skin surface of the arm and that is in communication with the reader device.

As an illustrative example, FIG. 2 illustrates, in cross-section, elements of a reader device 200, including the windings of a particular antenna coil 210 of an antenna array of the reader device 200. The reader device 200 is mounted to the surface of skin 205 proximate the location of an implanted device 207 within the skin. The implanted device 207 is located at a depth beneath the surface of the skin that is within a range of expected depths, indicated by $d_{min}$ and $d_{max}$. A mounting surface 245 of the reader device 200 is in contact with the skin 205. A contact layer 240 having a thickness $t_{superstrate}$ is disposed between the antenna coil 210 and the skin 205 and includes the mounting surface 245. The reader device 200 further includes a ground plane 220 that is separated from the antenna coil 210 by a spacing layer 230 having a thickness $t_{substrate}$. The reader device further includes a printed circuit board 250 (PCB) on which are disposed electronics 260. The electronics 260 are coupled, via traces 265 formed on the PCB 250, to the antenna coil 210, the ground plane 220, and other elements of the reader device 200 (not shown). Properties of the device 200 (e.g., a size or diameter of the coil 210, the thicknesses of the contact layer 240 and/or spacing layer 230) could be specified relative to the expected depth of the implanted device 207 beneath the skin (e.g., based on $d_{min}$ and $d_{max}$), the size of an antenna of the implanted device 207, or some other factors.

As shown, the antenna coil 210 is separated from the skin surface by a contact layer 240. The contact layer 240 could be configured to protect the antenna coil 210 from damage. The contact layer 240 could also have a thickness, dielectric constant, or other properties specified to prevent or reduce loading, detuning, or other effects of the skin 205 on electrical properties of the antenna coil 210. For example, the contact layer 210 could be composed of a low-loss material (e.g., a hydrocarbon/ceramic laminate material) to minimize dissipation of electromagnetic energy emitted by the coil 210. For example, the contact layer 240 could be composed of a material having a loss tangent that is less than approximately 0.002. Additionally or alternatively, contact layer 210 could have a low relative permittivity that is low, in order to maximize the efficiency of the antenna. For example, the contact layer could have a relative permittivity that is less than approximately 3.5.

In order to decrease detuning of the antenna coil 210 or other deleterious electrical effects of the skin 205 (e.g., of the relatively high relative permittivity or other electrical properties of the skin) on the performance of the antenna 210, the thickness of the contact layer 210 could be increased. However, increasing the thickness of the contact layer 240 could decrease coupling between the antenna coil 210 and the antenna of the implanted device 207 by increasing the distance between the implanted device 207 and the antenna coil 210. Thus, the thickness of the contact layer 240 could be specified based on a combination of factors (e.g., reducing distance to the implanted device 207 while minimizing the effects of the skin 205 on electrical properties of the antenna coil 210), e.g., the contact layer 240 could have a thickness between approximately 0.1 millimeters and approximately 0.4 millimeters. Alternatively, the contact layer 240 could be omitted from the reader device 200.

The illustrated reader device 200 includes a ground plane 220 separated from and substantially parallel to the antenna coil 210. The ground plane 220 could be composed of copper or some other conductive material. The ground plane 220 is separated from the antenna coil 210 by a spacing layer 230. The spacing layer could be composed of a low-loss material (e.g., having a loss tangent less than approximately 0.002) or otherwise specified (e.g., to have a low relative permittivity, e.g., less than approximately 3.5) to improve the electromagnetic coupling between the antenna coil 210 and the implanted device 207, to reduce an amount of energy emitted from the antenna coil 210 that is absorbed by the spacing layer 230, to increase an efficiency of the antenna coil 210, to minimize radiation of electromagnetic energy by vias 215 connecting the coil 210 to other elements of the device 200, or according to some other consideration.

The ground plane 220 and properties thereof (e.g., thickness, material composition, distance from the antenna coil 210) could be configured to increase the electromagnetic coupling between the antenna coil 210 and an antenna of the implanted device 207, e.g., by reflecting radio frequency waves emitted from the antenna 210 and/or the implanted device 207 (e.g., by being separated from the antenna coil 210 by a distance related to the wavelength of the emitted radio frequency waves and/or related to the size of the antenna coil 210). For example, if the diameter of the antenna coil 210 is between approximately 3 millimeters and approximately 3.5 millimeters, the ground plane could be greater than approximately 1.5 millimeters from the antenna coil 210 (that is, the spacing layer 230 thickness, $t_{substrate}$, could be greater than approximately 1.5 millimeters). The thickness of the spacing layer 230 could be increased with increases in the size of the antenna coil 210.

The ground plane could be formed to include a variety of structures, e.g., radio frequency resonators, reflectors, or other structures configured to improve transfer of radio frequency energy and/or transmissions between the antenna coil 210 and the implanted device 207. The reader device 200 could include additional ground plane layers and/or layers of formed resonators, reflectors, or other structures (e.g., disposed between the illustrated ground plane 220 and the antenna coil 210, disposed on the mounting surface 245 of and/or within the contact layer 240). Alternatively, the ground plane 220 could be omitted from the reader device 200.

The illustrated structures of the reader device 200 could be fabricated in a variety of ways. In some examples, the antenna coil 210, ground plane 220, and/or traces 265 could be formed via deposition, photo-patterning, or some other methods on a multi-layer printed circuit board. For example, the antenna coil 210 and ground plane 220 could be formed on opposite sides of a sheet of low-loss material and electrically and mechanically coupled to the PCB 250 on which the traces 265 are formed. In another example, the ground plane 220 and traces 265 could be formed on opposite sides of the PCB 250, and the spacing layer 230, antenna coil 210 (e.g., as one or more pieces of wire wound into a coil), and contact layer 240 could be disposed thereon. In a further example, the traces 265, PCB 250, ground plane 220, spacing layer 230, antenna coil 210, and contact layer 240 could be formed as a single multi-layer printed circuit board. In some examples, one or more of the illustrated structures could be a flexible material, such that an array of antenna coils that comprises the illustrated structures is flexible.

In some examples, one or more of the illustrated structures could be composed of a transparent material such that illumination can be delivered to the implanted device 207 and/or the skin 205 through such structures and/or such that light reflected by, scattered by, fluorescently absorbed and re-emitted by, or otherwise emitted by the implanted device 207 and/or skin 205 can be detected through such structures.

Additionally or alternatively, a window could be formed through one or more of the illustrated structures to allow illumination to be emitted through such windows and/or to allow light to be received form the implanted device 207 and/or skin 205 through such windows.

III. EXAMPLE IMPLANTABLE MICROELECTRONIC DEVICE

Reader devices described herein include an array of antenna coils configured to provide wireless (e.g., radio frequency) energy to, to transmit wireless transmissions to, to receive wireless transmissions from, or other otherwise wirelessly interact with implanted devices. Such implanted devices could include one or more antennas configured to receive such wireless power, to communicate wirelessly with the reader device, or to perform some other functions. Such implanted devices could include a variety of electronics configured to provide such functions and/or to provide further functions, e.g., to operate a sensor (e.g., a light sensor, an accelerometer, a strain sensor, an analyte sensor, a biopotential sensor) of the implanted device to measure a property and to transmit a wireless transmission related to the measured property and/or related to some other information (e.g., information about the identity or operational state of the implanted device, information about a cryptographic key, information about a user profile or user authentication information).

Such implanted devices could have a very small size (e.g., could have a largest dimension that is less than approximately 1 millimeter). Thus, implanted devices as described herein could be described as microelectronic devices. Such microelectronic devices could include logic gates, microcontrollers, or other digital logic elements configured to be powered by wireless power received from a reader device and/or to generate wireless transmissions to the reader device. Alternatively, implanted devices as described herein could include only analog components (e.g., resonators, variable capacitors having a capacitance related to a physical variable of interest, surface acoustic wave transducers and/or filters). In some examples, components (e.g., electronics, sensors, antennas) of such implanted devices could be enclosed within a protective and/or encapsulating shell or layer, e.g., glass, to protect the components from the environment within a body and/or to improve the biocompatibility of the implanted device.

A microelectronic implanted device as described herein (e.g., 120, 207) could be formed by a variety of processes such that the microelectronic device has a small size (e.g., a largest dimension less than approximately 0.4 millimeters). In some examples, this could include forming most or all of the elements of the microelectronic device on or within a single integrated circuit (e.g., an integrated circuit having an area of less than approximately 400 microns by less than approximately 400 microns and a thickness less than approximately 100 microns). That is, a sensor, an energy receiver, a transmitter, a controller, and/or some other elements of the microelectronic device could be provided in a single integrated circuit. In some examples, additional components could be formed on and/or adhered or connected to such an integrated circuit. For example, a coil or other antenna structure(s) could be electrically connected to and/or wound around the periphery of such an integrated circuit. Further, a layer of protective, biocompatible, analyte-sensitive, or otherwise configured material could be formed on one or more surfaces of such an integrated circuit (e.g., to encapsulate the integrated circuit) to provide some functions, e.g., to control an interface between the integrated circuit and tissue into which the integrated circuit is implanted or otherwise disposed. In some examples, a microelectronic device could be formed from multiple integrated circuits reflow-soldered, adhered with an adhesive, or otherwise bonded together (e.g., a first integrated circuit that includes a controller and a sensor bonded to a second integrated circuit that includes an energy receiver, a transmitter, and an antenna coil electronically connected to the energy receiver and transmitter).

Figure 3A:
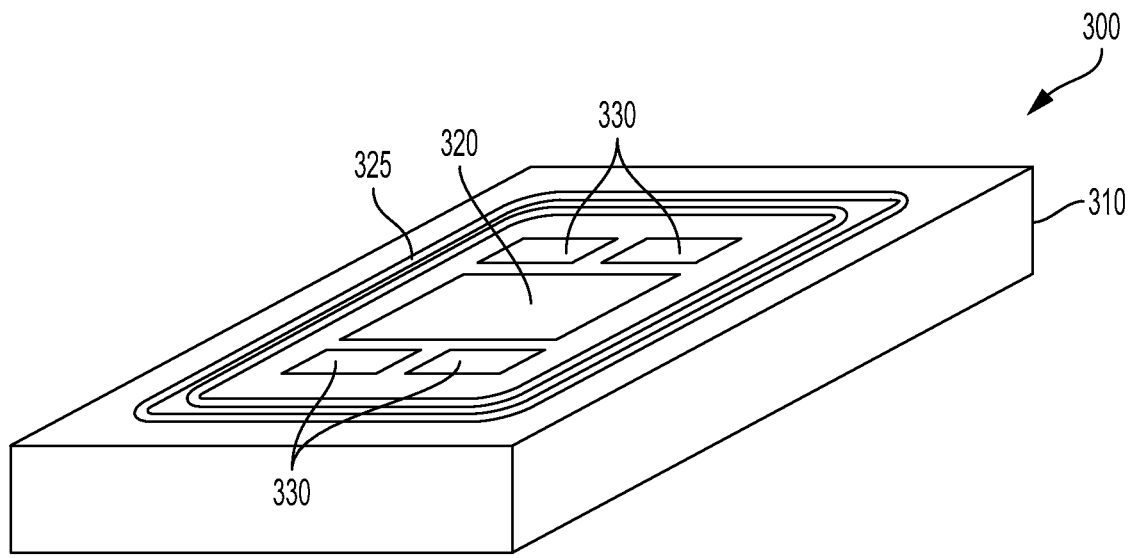
FIG. 3A is a perspective view of an example microelectronic device.
Figure 3B:
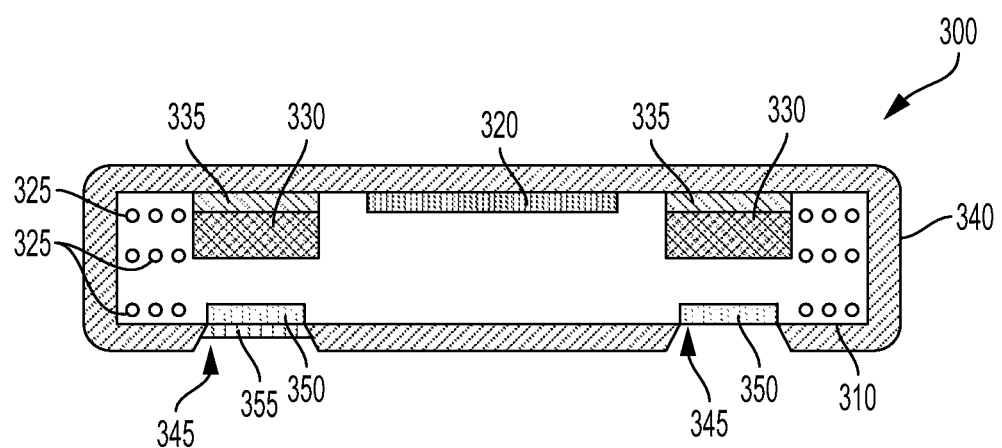
FIG. 3B is a cross-sectional view of the example microelectronic device shown in FIG. 3A.

As an illustrative example, FIGS. 3A and 3B show (in a perspective view and a cross-sectional view, respectively) an implantable microelectronic device 300 that comprises a single integrated circuit 310 (e.g., an integrated circuit formed from a single piece of silicon or some other semiconductor or other integrated circuit substrate material). A variety of components of the microelectronic device 300 are formed from the integrated circuit 310. These components include an antenna coil 325, a photovoltaic cell 320, a number of light sensors 330 (e.g., photodiodes, phototransistors, some other optoelectronic elements), and first and second electrodes 350. The microelectronic device 300 further includes, formed on the surface(s) of the integrated circuit 310, optical filters 335, an encapsulation layer 340, and an analyte-sensitive substance 355.

The coil 325 could be configured to receive wireless energy (e.g., radio frequency energy transmitted from a reader device or other external system) to power the microelectronic device 300. Additionally or alternatively, the coil 325 could be configured to receive and/or transmit wireless transmissions from/to an external system or device (e.g., from/to an antenna coil of an array of antenna coils of a reader device as described elsewhere herein). The coil could be operated to emit wireless indications by controlling a pattern over time of an amount of received radio frequency energy that is backscattered or otherwise reflected by the coil 325. This could include detuning the coil 325 or otherwise controlling one or more electrical properties of the coil 325, over time, by connecting a specified impedance to the coil 325 (e.g., by operating an electrical switch to connect a specified low or high impedance across two terminals of the coil 325). As shown, the coil 325 in includes multiple turns of conductive material (e.g., polysilicon, metallic traces, some other conductive material) formed in multiple layers. Alternatively, a coil could include a single turn formed in multiple layers (e.g., an effectively helical coil), a number of turns formed in a single layer (e.g., a spiral coil), or some other shape or configuration. Further, the microelectronic device 300 could include striplines, fractal antennas, patch antennas, or some other formed elements configured to transmit or receive wireless transmissions and/or to receive wireless energy to power the microelectronic device 300.

Additionally or alternatively, the microelectronic device 300 could include an LED, laser, or other optoelectronic element(s) (not shown) configured to provide optical wireless indications (e.g., by controlling a pattern over time of an intensity, wavelength, polarization degree or direction, or some other property of an emitted optical energy over time).

The photovoltaic cell 320 is configured to receive optical energy to power the microelectronic device 300. Further, the photovoltaic cell 320 could be used as a light sensor to detect an intensity or other property of light received by the photovoltaic cell 320 (e.g., to detect an intensity of light transmitted through a portion of subsurface vasculature and received by the photovoltaic cell 320). This could include detecting a current, or voltage produced by the photovoltaic cell 320.

The light sensors 330 each include one or more of a photodiode, phototransistor, photoresistive element, or other light-sensitive element(s). The light sensors 330 can detect the intensity of light having a specified wavelength, polarization, direction of incidence, or some other property of light. In some examples, this could include light-sensitive elements of the light sensors 330 being sensitive to the intensity of received light and the optical filters 335 being configured to block light that has a wavelength, polarization direction, or other property that does not correspond to a specified range of wavelengths, polarization directions, or other properties such that the intensity detected by the light-sensitive elements corresponds to the intensity of light within the specified range of wavelengths, polarization directions, or other properties. For example, the optical filters 335 could include Bragg reflectors, color filters, or other elements configured to pass light within a specified range of wavelengths. In another example, the optical filters 335 could include gratings or other elements configured to pass light that is incident from within a specified range of angles relative to the microelectronic device. The optical filters 335 could be formed from the integrated circuit 310 (e.g., could be formed from a plurality of conductive traces to form a grating, a plurality of layers of materials having different dielectric constants to form a Bragg reflector). Additionally or alternatively, the optical filters 335 could be formed on or adhered to the integrated circuit 310, e.g., by sputtering or other deposition techniques, by formation in a process separate from the integrated circuit 310 and being subsequently adhered to the integrated circuit 310 by an adhesive or some other means, or according to some other process.

As shown, the microelectronic device 300 includes a number of different light sensors 330. The light sensors 330 could be configured to detect substantially the same property of light (e.g., the intensity of received light within a specified range of wavelengths from substantially the same range of incident angles relative to the microelectronic device 300) that is received at different locations of the microelectronic device (e.g., locations corresponding to the locations of the light sensors 330). In such examples, the outputs of the different light sensors 330 could be used to map the intensity of light across a surface of the microelectronic device 300, to determine a gradient of the light intensity, to determine a relative absorption of light by a portion of subsurface vasculature proximate the microelectronic device 300 (e.g., by comparing the intensity of light received by a light sensor 330 beneath the portion of subsurface vasculature to the intensity of light received by a light sensor 330 that is not beneath the portion of subsurface vasculature), or to perform some other determination or function. Additionally or alternatively, different lights sensors 330 could be configured to detect light within different ranges of wavelengths, from different incident directions, or that differs according to some other property. For example, a first light sensor 330 could be configured to detect light of a first wavelength (e.g., a red wavelength) that is transmitted through a portion of subsurface vasculature and a second light sensor 330 could be configured to detect light of a second wavelength (e.g., a near-infrared wavelength) that is transmitted through the portion of subsurface vasculature and an oxygen content or saturation of the blood in the portion of subsurface vasculature could be determined based on the intensity of light detected by the first and second light sensors 330.

The first and second electrodes 350 could be configured and/or operated in a variety of ways to provide detection of biopotentials (e.g., voltages and/or currents related to an electromyogram, an electrocardiogram, or signals related to other electrically active cells of a body), to detect the concentration of an analyte (e.g., hydronium ions, potassium, glucose), or to provide some other function. The first and second electrodes 350 could be formed of a metallic and/or conductive material (e.g., polysilicon, aluminum, gold) during the formation of the integrated circuit 310. Additionally or alternatively, a layer of silver, silver chloride, platinum, gold, or some other material could subsequently be formed (e.g., by sputtering, by electroplating) on the surface of the electrodes 350.

In some examples, the electrodes 350 could be configured and/or operated to detect an analyte in interstitial (or other fluid) within skin or some other tissue within which the microelectronic device 300 is disposed. The electrodes 350 could detect the analyte electrochemically, e.g., by detecting a voltage between and/or a current passing through the electrodes 330 that is related to the concentration, presence, or some other property of the analyte. Thus, one of the electrodes 350 could be configured to act as a working electrode, with an immobilized analyte-sensitive substance 355 (e.g., a reagent, a protein, an enzyme) that selectively interacts with the analyte on or near the working electrode. Such an analyte-selective substance can be immobilized on the surface of the working electrode by crosslinking the substance into a crosslinked layer on the surface of the electrode. This could include using an aldehyde, dialdehyde (e.g., glutaraldehyde), or other crosslinking agents to form the crosslinked layer of the substance on the electrode surface. Additionally or alternatively, such an analyte-selective substance can be localized within an analyte-permeable polymer layer that is disposed on the working electrode.

The protective layer 340 is provided to protect the integrated circuit 310 from a tissue environment (e.g., from damage caused by a foreign body response), to protect tissues from the integrated circuit 310 (e.g., to prevent cytotoxic chemicals and/or surfaces of the integrated circuit 210 from damaging the tissue and/or emitting harmful chemicals into a body), to reduce and/or control a foreign body response of a body to the presence of the microelectronic device 200, or to provide some other functionality. As shown, the protective layer 340 includes windows 345 formed through the protective layer 340 to allow fluids and/or tissues in the environment of the microelectronic device 300 to contact the electrodes 350 and/or the analyte-sensitive substance 355. The protective layer 340 could include further windows or other features, e.g., to provide access to further sensors (e.g., electrodes, pressure sensors, analyte or fluid sensors), to provide means for mounting the integrated circuit 310 (e.g., attaching a suture or other connecting means to holes, tabs, or other formed features of the protective layer 340), or according to some other application.

The integrated circuit 310 further includes electronics (not shown) configured to operate the elements of the microelectronic device 300 to receive wireless power from an external source (e.g., to receive optical, radio frequency, or some other form of energy from an external reader device or some other power source), to detect physical variables and/or determine hemodynamic or physiological parameters of a body within which the microelectronic device 300 is disposed, to provide wireless transmissions of detected properties or parameters, and to provide other functions of the microelectronic device 300. Such a controller could include analog elements (e.g., amplifiers, filters, buffers, power conditioning circuits, analog oscillators), digital elements (e.g., analog-to-digital converters, microprocessors, comparators, logic gates, digital oscillators, memories), or other components configured to provide functions of the microelectronic device 300.

In some examples, operation of sensors of the device 300 (e.g., light sensors 330, photovoltaic cell 320) to generate signals related to a property or parameters of interest and generation of wireless indications related thereto could involve substantially analog operations. For example, a current, voltage, or other signal generated by a sensor could be applied to control the frequency of an analog voltage-controlled oscillator. The output of the analog voltage-controlled oscillator could be applied (e.g., via an amplifier, mixer or other elements) to generate radio-frequency signals that have a frequency or other property related to the signal output by the sensor and that are transmitted by the coil 325 or some other transmitting and/or radiating means. In another example, a current, voltage, or other signal generated by a sensor could be applied to control an impedance of the coil 325 (e.g., by controlling a capacitance of a voltage-controlled capacitor that is connected to the coil, by controlling an analog switch configured to connect an impedance to the coil 325 to detune the coil 325). An effective impedance, quality factor, or other property of the coil 325 that is thus related to the signal output by the sensor could be detected by emitting radio frequency energy toward the coil 325 (e.g., by an antenna, coil, or other emitting means of an external reader device) and detecting an amount, a phase, or some other property of the emitted energy that is reflected, backscattered, or otherwise responsively emitted by the coil 325.

Additionally or alternatively, operation of sensors of the device 300 (e.g., light sensors 330, photovoltaic cell 320) to generate signals related to a property or parameters of interest and generation of wireless indications related thereto could involve digital operations. For example, an analog-to-digital converter of the device 300 could be operated to generate one or more digital codes related to a current, voltage, or other signal generated by a sensor of the microelectronic device 300. A microcontroller or other digital elements of the microelectronic device 300 could then control over time the intensity, phase, frequency, polarization degree or detection, or other properties of an emitted radio frequency, optical, or other wireless indication generated, reflected, backscattered, or otherwise emitted by indicating means (e.g., a coil, an antenna, a light-emitting diode, a laser, a liquid crystal, an electronic paper element) of the microelectronic device 300 to provide an indication related to (e.g., including an encoding in time-variations of the intensity or other properties of the emitted indication) the generated digital code. Further, such a microcontroller (or other digital elements of the microelectronic device 300) could operate to store such digital codes in a memory for later use (e.g., wireless indication at a later time), to determine a physiological or hemodynamic parameter based on one or more such digital codes (e.g., to determine an oxygen content of blood base on to or more detected intensities of light transmitted through a portion of subsurface vasculature), to provide an indication related to such determined parameters, or to perform some other operations.

Note that the illustrated microelectronic device 300 is intended as a non-limiting example. Microelectronic devices as described herein could include more or fewer of the illustrated elements or could include additional elements (e.g., additional types of sensors, additional means for providing wireless indications). For example, a microelectronic device could wholly or partially enclose a portion of subsurface vasculature, e.g., could include a strain-sensitive extension configure to at least partially enclose a portion of subsurface vasculature such that expansion of the portion of subsurface vasculature (e.g., related to a pressure in the portion of subsurface vasculature, related to a volume of blood in the portion of subsurface vasculature) could deform the strain-sensitive extension, allowing the microelectronic device to detect a strain that is related to hemodynamic properties of the portion of subsurface vasculature.

Moreover, it is particularly noted that while sensors and implantable microelectronic devices including such sensors are described herein by way of example as a devices configured to be implanted beneath a skin surface of a person (e.g., proximate a portion of subsurface vasculature), it is noted that the disclosed microelectronic devices can be applied in other contexts as well. For example, microelectronic devices disclosed herein may be included in implantable devices used to measure a hemodynamic or physiological parameter or other information relating to an animal. In another example, microelectronic devices disclosed herein may be included in devices to measure a light intensity or other properties of a natural environment, a material or fluid that is part of an artificial process, such as a waste treatment process, pharmaceutical synthesis process, food preparation process, fermentation process, or medical treatment process, or to measure a light intensity or other properties of some other material or environment. Further, reader devices as described herein (i.e., reader devices including arrays of antenna coils configured to interact with such microelectronic devices) could be configured to be mounted to surfaces of and/or within such alternative environments.

IV. EXAMPLE ELECTRONICS OF A READER DEVICE

Figure 4:
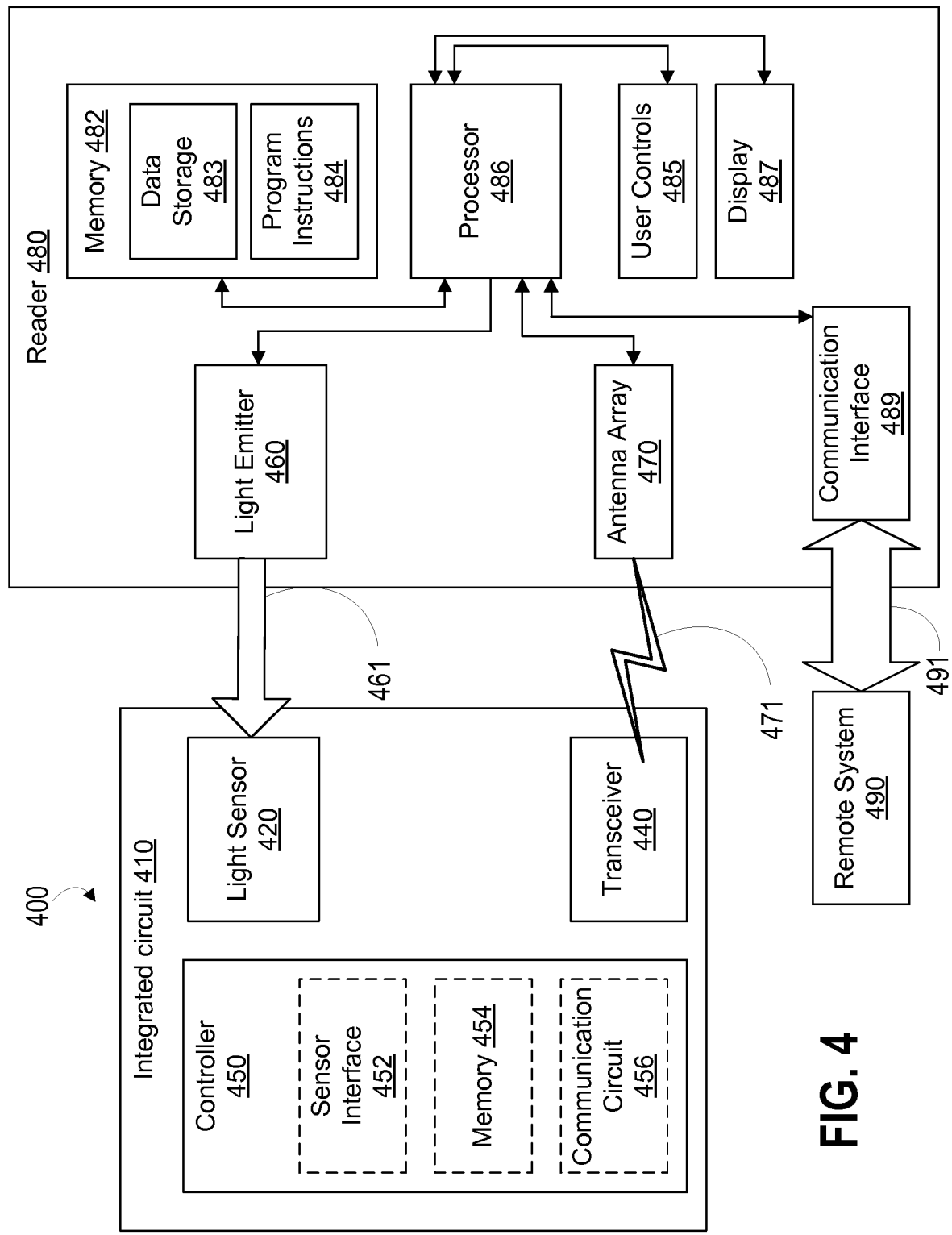
FIG. 4 is a block diagram of an example system that includes a microelectronic device in wireless communication with an external reader.

FIG. 4 is a block diagram of a system that includes an implanted microelectronic device 400 in wireless communication with an external reader device 480. The microelectronic device 400 includes a single integrated circuit 410 that provides one or more elements of the microelectronic device 400 (e.g., electronics, sensors, transmitters, energy receivers) and that is configured to be implanted or otherwise placed beneath a skin surface, e.g., such that a portion of subsurface vasculature is located between the microelectronic device 400 and the skin surface. As illustrated, the integrated circuit 410 provides a light sensor 420, a transceiver 440, and a controller 450. The transceiver 440 supplies operating voltages to the controller 450 and/or other elements of the microelectronic device 400 by receiving wireless energy 471 from the external reader 480 and/or transmits wireless transmissions 471 to the external reader 480, via an antenna array 470. The light sensor 420 is configured to detect a property (e.g., an intensity) of light received from the environment of the microelectronic device 400, e.g., light that has been reflected by, scattered by, partially absorbed by, or otherwise transmitted through a portion of subsurface vasculature. Such light can be provided as illumination 461 provided by a light emitter 460 of the external reader 480, or can be provided from ambient light sources or some other source of illumination. The transceiver 440 can be operated by the controller 450 to provide wireless indications (e.g., radio frequency indications 471) related to information detected or determined using the light sensor 420 and/or related to some other information.

As shown, the transceiver 440, the controller 450, and the light sensor 420 are provided by the integrated circuit 410. However, one or more of these components, or elements thereof, could be attached to and/or formed on the integrated circuit 410 and/or provided in one or more further integrated circuits (e.g., one or more further integrated circuits soldered to, adhered to with an adhesive, or otherwise bonded to and electrically connected with the integrated circuit 410). For example, a coil or other antenna of the transceiver 440 could be provided as a loop of wire or other conductive elements formed on or otherwise disposed on the integrated circuit 410. In some examples, such elements, or further integrated circuits, could be connected to the integrated circuit 410 via one or more pads formed on the surface of the integrated circuit 410. Further, the integrated circuit 410 could be coated in a protective layer (e.g., a layer of polymer) or some other material covering to protect the integrated circuit 410, to control the interface between the microelectronic device 400 and surrounding tissues or fluids, to sensitize a sensor (e.g., an electrode) of the integrated circuit to an analyte of interest, to control a property of light received from the environment by the light sensor 420 (e.g., by forming and/or disposing an optical filter on the integrated circuit 410 over the light sensor 420).

The controller 450 formed in the integrated circuit 410 could include a variety of elements. For example, the controller 450 could include logic gates, arithmetic logic units, microprocessors, registers, digital oscillators, counters, logical buses, amplifiers, analog-to-digital converters (ADCs), mixers, analog oscillators, buffers, or some other component or components. Such components can be electrically connected via interconnects or traces formed (e.g., patterned) on or within the integrated circuit 410. The controller 450 can include analog components (e.g., amplifiers, buffers, current sources), logic elements (e.g., comparators, counters, digital clocks or oscillators), or other components (e.g., ADCs) configured to operate the light sensor 420 to detect the intensity or some other property of a received light, an encoder, modulator, mixer, amplifier, or other elements configured to provide wireless indications (e.g., light intensity levels, digital codes generated by an ADC, determined physiological or hemodynamic parameters) via the transceiver 440, and/or to provide other functions.

The transceiver 440 can be configured to receive wireless energy (e.g., radio frequency energy) from an antenna of the antenna array 470 to power the microelectronic device 400. In such examples, the transceiver 440 could include a loop antenna (e.g., a loop antenna formed from one or more layers and/or loops of conductive material formed one or within the integrated circuit 410 and/or formed from one or more loops of wire or other conductive material formed and/or disposed on the integrated circuit 410) that is configured to receive RF energy from the external reader 480. In some examples, such an RF-energy-receiving antenna can also be used to communicate with external devices by, e.g., transmitting a wireless transmission. Additionally or alternatively, the microelectronic device 400 could include a photovoltaic cell, a photodiode, or some other means for receiving optical energy. Such optical energy could be ambient light provided by the environment of the microelectronic device 300, e.g., via the surface of skin beneath which the microelectronic device is implanted or otherwise disposed. In some examples, such optical energy could be provided by a light emitter (e.g., an infrared, visible, or ultraviolet light emitter) of an external device (e.g., light emitter 460 of reader device 480) that is configured to provide optical energy to the microelectronic device 400. In such examples, the optical energy emitted by the external device could have a specified wavelength (e.g., a wavelength that is minimally absorbed by blood and/or tissues in the skin) and the optical energy receiving element(s) (e.g., a photodiode or photovoltaic cell) of the microelectronic device 400 could be configured to efficiently receive the emitted optical energy and to provide the received energy to power the microelectronic device 400.

The sensor interface module 452 could take a variety of forms according to the methods used to detect properties of light received by the light sensor 420 and/or the configuration or operation of further sensors of the microelectronic device 400 (not shown) used to detect other physical variables related to physiological and/or hemodynamic parameters of interest. The light sensor 420 could include a photodiode, a phototransistor, a photoresistive element, or some other components configured to output a voltage, a current, or some other electrical signal related to the intensity of a received light, the intensity of a received light within a specified range of wavelengths, the intensity of received light within a specified range of polarizations, the intensity of light received from a specified range of incident angles relative to the microelectronic device 400, or to detect some other properties of received light. The sensor interface module 452 could include amplifiers, transimpedance amplifiers, filters, buffers, voltage references, ADCs, or other components configured to operate the light sensor 420 (or some other sensor(s)) to output a signal (e.g., to generate one or more digital codes) related to the detected property of light received by the light sensor 420.

Additional or alternative sensors can be operated by the sensor interface module 452. Such sensors could include temperature sensors, strain sensors, accelerometers, gyroscopes, pressure sensors, electric or magnetic field sensors, electrodes or other elements configured to detect a potential and/or current between two or more locations of tissue or fluid that are in contact with the electrodes, analyte sensors, or some other types of sensors.

The sensor interface 452 can include an ADC configured to receive an electrical signal that is generated by the light sensor 420 (or some other sensor of the microelectronic device 400) and/or elements of the sensor interface 452 that are related to a hemodynamic and/or physiological parameter, e.g., to a blood flow rate, a blood oxygenation, a volume of blood in skin, or some other physical variable, and generate a digital code. The electrical signal could be a signal generated by an electrode, an amplifier, a buffer, a photodetector, a multiplexer, or some other electronic component(s) of the microelectronic device 400. Further, the generated digital code could be related to a voltage, current, frequency, pulse rate, inter-pulse interval, or some other property of the electrical signal. The ADC could include a direct-conversion ADC, a successive approximation ADC, a ramp-compare ADC, a pipeline ADC, a sigma-delta ADC, or some other type of ADC and/or electronic components configured to generate digital codes based on properties of received electrical signals. Additionally or alternatively, a signal related to a property of interest could be used by analog electronics of the device 400 (e.g., to control a voltage-controlled oscillator to control a frequency, phase, or other property of a wireless transmission transmitted by the transceiver 440) to provide an indication related to a property of interest.

The controller 450 could be configured to determine values of a detected physiological parameter (e.g., a pulse rate, a blood oxygen content) based on one or more digital codes or other signals generated by the sensor interface 452. For example, the controller 450 could include digital adders, multipliers, arithmetic logic units, programmable gate arrays, registers, accumulators, barrel shifters, or other logical elements configured to perform computations on generated digital codes in order to determine values of related physiological parameters. The device 400 could be operated to determine one or more values of the physiological parameter (e.g., pulse rates, blood oxygen contents) in response to a variety of factors or other considerations. For example, the device 400 could receive a communication from another system (e.g., from the external reader 480 using the communication circuit 456) requesting a value of the physiological parameter (e.g., a reader 480 could transmit a wireless signal using an antenna coil of the antenna array 470, light emitter 460, or some other components that indicates such a request) and the controller 450 could responsively determine a value of the physiological parameter and wirelessly indicate such a value using the transceiver 440. Additionally or alternatively, the microelectronic device 400 could operate to provide wireless transmissions, to operate the light sensor 420 or some other sensors to detect a physical variable, to determine a physiological parameter based on such sensor operations, or to perform some other functions in response to receiving power from the antenna array 470 using the transceiver 440.

The memory 454 could include a variety of volatile and nonvolatile electronic storage elements configured to provide means for the microelectronic device 400 to record and/or log information (e.g., digital codes) related to a detected and/or determined physiological property (e.g., related to intensities of received light, related to a blood oxygen content), calibration information, and/or other information detected by or input to the microelectronic device 400. For example, the memory 454 could include one or more EEPROM memories, flash memories, NVRAM memories, DRAM memories, SRAM memories, flip-flops, or other information storage elements. The memory 454 could have an information storage capacity sufficient to record some specified period of information detected using the light sensor 420 (e.g., digital codes generated based on a signal generated by the light sensor 420) at some specified rate of detection. Additionally or alternatively, the microelectronic device 400 could be in communication with a memory that is external to the microelectronic device 400 and that could be used as described above (e.g., to store generated digital codes, to store and/or access calibration or other configuration data of the microelectronic device 400).

The controller 450 includes a communication circuit 456 for providing wireless transmissions to an antenna coil of the antenna array 470 via the transceiver 440. The communication circuit 456 can optionally include one or more oscillators, mixers, frequency injectors, etc. to modulate and/or demodulate information on a carrier frequency to be transmitted as a radio frequency indication by a coil, antenna, or other elements of the transceiver 440. In some examples, the microelectronic device 400 is configured to transmit information (e.g., generated digital codes, values of a physiological parameter determined therefrom) by modulating an impedance of an antenna (e.g., a loop antenna or coil) of the transceiver 440 in a manner that is perceivable by an antenna coil of the antenna array 470 of the external reader 480. For example, the communication circuit 456 can cause variations in the amplitude, phase, and/or frequency of backscatter radiation from the antenna of the transceiver 440, and such variations can be detected by an antenna coil of the antenna array 470. Such wireless communication could be compatible with one or more existing backscatter wireless communications standards, e.g., RFID. Additionally or alternatively, the communication circuit 456 and transceiver 440 could be configured to transmit wireless signals according to some other method, e.g., according to the Bluetooth (e.g., Bluetooth Low Energy), ZigBee, WiFi, LTE, and/or some other wireless communications standard or scheme. In some examples, such communications (e.g., data transmitted from the microelectronic device 400) could be cryptographically secured; that is, the wireless communications link could be encrypted.

It is noted that the block diagram shown in FIG. 4 is described in connection with functional modules for convenience in description. However, embodiments of the microelectronic device 400 can be arranged with one or more of the functional modules ("sub-systems") implemented in a single integrated circuit (e.g., 410), multiple integrated circuits physically and electrically bonded together, one or more loops of wire or other elements formed and/or disposed on such an integrated circuit(s), or according to some other consideration.

The external reader 480 includes an antenna array 470. The antenna array includes a plurality of antenna coils that span a specified area (e.g., of a skin surface beneath which the microelectronic device 400 is disposed) and that have respective degrees of electromagnetic coupling with an antenna of the transceiver 440. The antenna array 470 is operable to select an antenna coil of the array 470 (e.g., using a radio frequency switch) and to operate the selected antenna coil to at least one of (i) receive wireless transmissions 471 from or (ii) provide wireless power 471 to the microelectronic device 400 via an antenna of the trajectories 440. In some examples, an antenna used to provide radio frequency energy to the microelectronic device 400 could additionally be used to detect an amount of the transmitted radio frequency energy that is backscattered or otherwise reflected by the microelectronic device 400 to provide a wireless transmission of information to the reader device 480. The antenna array 470 and/or antenna coils thereof could be configured to perform further functions, e.g., to transmit wireless transmissions to the microelectronic device 400, to detect the location, orientation, or depth of the microelectronic device 400, or some other functions.

The external reader 480 further includes a light emitter 460. The light emitter 460 is configured to provide illumination 461 that can be received by the light sensor 420 of the microelectronic device 400. The light emitter 460 could include one or more LEDs, lasers, or other light-emitting elements configured to emit light having a specified wavelength, spectral content, degree or direction of polarization, coherence length, or some other property specified according to an application. Such illumination could be scattered by, partially absorbed by, fluorescently absorbed and re-emitted, reflected by, or otherwise transmitted through a portion of subsurface vasculature or other tissue or target of interest. A property of such interaction between the emitted light and the target of interest (e.g., blood in a portion of subsurface vasculature) could be detected by the light sensor 420, e.g., to determine one or more properties of the target. For example, an amount of absorption of light by blood in a portion of subsurface vasculature at one or more wavelengths could be related to a volume of blood in the portion of subsurface vasculature, an oxygen content of the blood, or some other properties. Additionally or alternatively, a time-varying pattern of constructive and destructive interference in coherent light scattered by or otherwise transmitted through blood in a portion of subsurface vasculature could be related to the velocity (e.g., a distribution of velocities) of blood cells flowing in the portion of subsurface vasculature. The light emitter 460 could emit light continuously, in pulses, or according to some other pattern. Further, the light emitter 460 could be operated to optically indicate information, e.g., in a coded pattern of light pulses, that could be detected by the controller 450 using the light sensor 420.

In some examples, the light emitter 460 could comprise an array of light emitters. Each light emitter of such an array could be configured to provide illumination to a corresponding portion of tissue (e.g., skin, subsurface vasculature) proximate the reader device 480 and to implanted devices (e.g., 400) therein. Such light emitters could be configure dot provide illumination to optically power the implanted device 400, to illuminate the light sensor 420, to provide optical transmissions (e.g., commands, programming) to the implanted device 400, or to provide some other functions. Light emitters of such an array of light emitters 460 could be selected to maximize the efficiency of optical power transfer, to optimize optical detection, using the light sensor 420, of some physiological parameter, to minimize an amount of light exposure of tissue, or according to some other consideration. In some examples, each antenna coil of the array of antenna coils 470 could be associated with one or more of the light emitters of such an array of light emitters 460. Selection of a particular antenna coil could include selection of the associated light emitters, which could be operated to provide illumination. In some examples, the association between light emitters and antenna coils could be one-to-one (that is, the light emitter array 460 could include one light emitter for each antenna coil of the array of antenna coils 470). Alternatively, each antenna coil could be associated with more than one light emitter (e.g., a set of light emitters disposed along the edge of the antenna coil) and/or each light emitter could be associated with more than one antenna coil (e.g., a set of antenna coils neighboring or otherwise proximate to the antenna coil). The external reader 480 also includes a computing system with a processor 486 in communication with a memory 482. The external reader 480 can also include one or more of user controls 485, a display 487, and a communication interface 489. The memory 482 is a non-transitory computer-readable medium that can include, without limitation, magnetic disks, optical disks, organic memory, and/or any other volatile (e.g. RAM) or non-volatile (e.g. ROM) storage system readable by the processor 486. The memory 482 can include a data storage 483 to store indications of data, such as sensor readings (e.g., generated digital codes and/or values of the physiological property determined therefrom that are related to signals generated using the light sensor 420), program settings (e.g., to adjust behavior of the microelectronic device 400 and/or external reader 480), etc.

The memory 482 can also include program instructions 484 for execution by the processor 486 to cause the external reader 480 to perform processes specified by the instructions 484. For example, the program instructions 484 can cause external reader 480 to perform any of the functions described herein. For example, program instructions 484 may cause the external reader 480 to provide a user interface that allows for retrieving information communicated from the microelectronic device 400 (e.g., digital codes generated by the sensor interface 452, values of a physiological parameter determined therefrom by the controller 450) by displaying that information on the display 487 in response to commands input through the user controls 485. The external reader 480 can also include one or more hardware components for operating the antenna array to select an antenna coil of the antenna array 470, to receive the wireless transmissions 471 from the microelectronic device 400 using the selected antenna coil, to provide wireless energy 471 to at least partially power the microelectronic device 400 using the selected antenna coil, or to perform some other functions (e.g., to transmit a wireless transmission to the microelectronic device 400). The external reader 480 can also include one or more hardware components for operating the light emitter 460 to illuminate 461 a target of interest (e.g., a portion of subsurface vasculature), or to perform some other operations.

The external reader 480 can also be configured to include a communication interface 489 to communicate signals via a communication medium 491 to and from a remote system 490. For example, the remote system 490 may be a smart phone, tablet computer, laptop computer, or personal computer, and communication interface 489 and communication medium 491 may be a Bluetooth module and wireless Bluetooth communication signals, respectively. In this example, the external reader 480 may be configured to send information about the physiological parameter or other information detected or determined by the microelectronic device 400 to the smart phone, tablet computer, laptop computer, or personal computer for storage and offline analysis. In another example, the remote system 490 is a server at a clinic or physician's office, the communication interface 489 is a WiFi radio module, and the communication medium 491 is a network sufficient to enable the transfer of data between the remote server and the WiFi radio module. A physician may use this data to make determinations or diagnoses related to the subject's condition. Further, the external reader 480 may be configured to receive signals from a remote server, such as instructions sent by a physician at a remote location to, for example, increase or decrease sampling frequency. Communication interface 389 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 480 can be a smart phone, digital assistant, or other portable computing device with wireless connectivity sufficient to provide the wireless communication link 471 and/or wireless power 471. The external reader 480 can also be implemented as an antenna array module that can be plugged in to a portable computing device, such as in an example where the wireless communication link 471 and/or wireless power 471 include electromagnetic fields and/or waves at carrier frequencies not commonly employed in portable computing devices. In some instances, the external reader 480 is a special-purpose device configured to be periodically placed relatively near the microelectronic device 400 to allow the wireless communication link 471 and/or wireless power link 471 to operate with a low power budget.

As described elsewhere herein, a particular antenna coil of an array of such antenna coils (e.g., 140, 470) can be selected and operated to provide wireless power to an implanted device, to receive wireless transmissions from such an implanted device, or to perform some other operations. Such an antenna array and/or antenna coils thereof can be configured in a variety of ways to provide this functionality. In some examples, each of the antenna coils could be coupled to a respective receiver and/or transmitter, and selection of a particular antenna coil could include selecting and operating the receiver and/or transmitter of the selected antenna coil while disabling or otherwise operating receivers and/or transmitters of non-selected antenna coils. For example, receivers and/or transmitters of non-selected antenna coils could be operated to connect the non-selected antenna coils to respective specified high impedances (e.g., to electrically disconnect the non-selected antenna coils from other components) or specified low impedances (e.g., to electrically short the terminals of the non-selected antenna coils) to, e.g., prevent the non-selected antenna coils from interfering with the operation of the selected antenna coil to provide wireless power, to receive wireless transmissions, or to perform some other functions.

Figure 5:
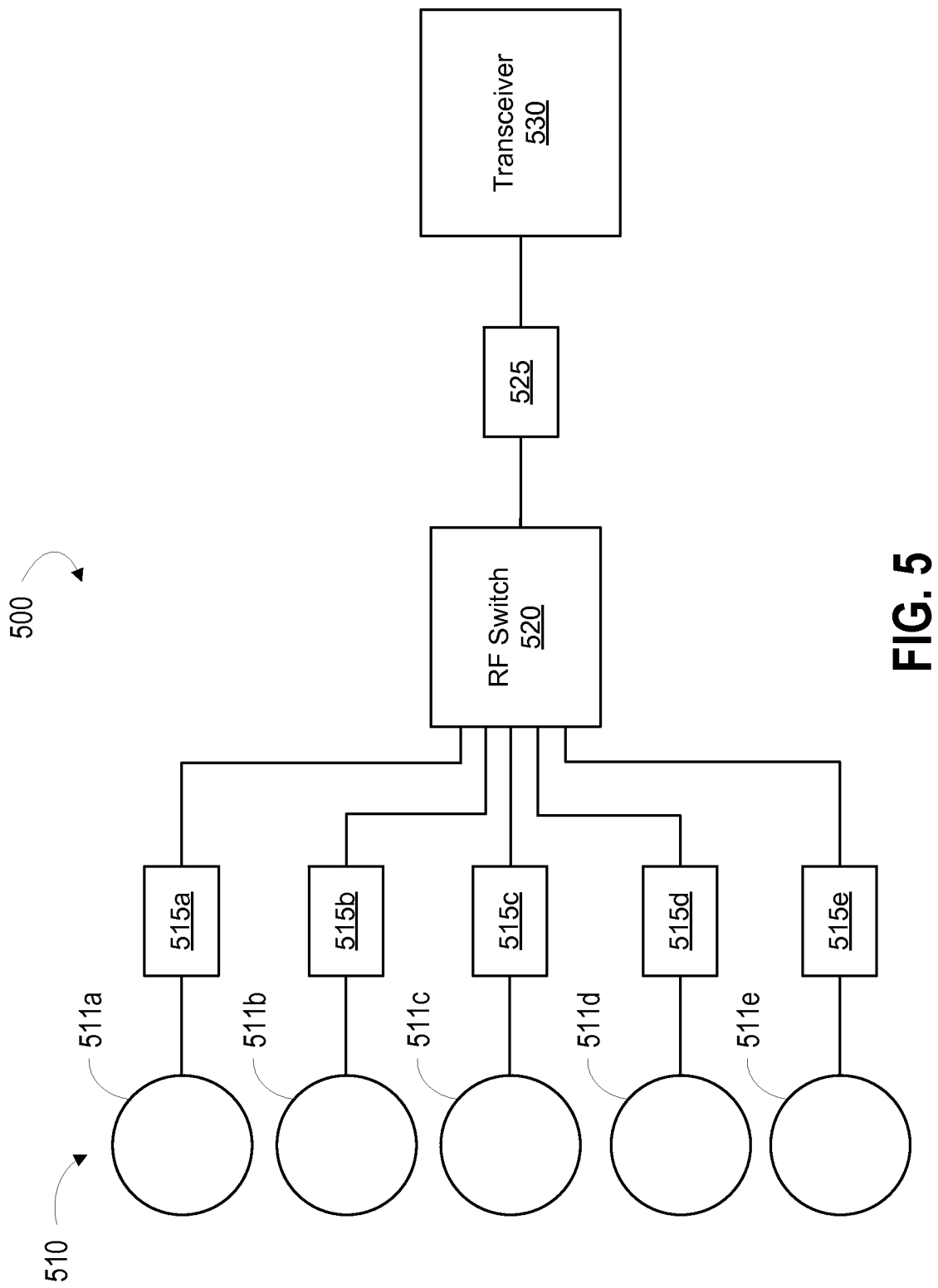
FIG. 5 is a block diagram of an example system that includes an antenna array that can be operated to communicate with a microelectronic device.

Additionally or alternatively, all of the antenna coils of an antenna array (or a subset of the antenna coils of an antenna array) could be coupled, via a radio frequency (RF) switch, to a receiver and/or transmitter. In such an example, operating a selected antenna coil could include operating the RF switch to couple the selected antenna coil to the receiver and/or transmitter. To illustrate this, FIG. 5 shows elements of a reader device 500. The elements include antenna coils 551a-e of an array of antenna coils 510 (that is, e.g., configured to span a specified area of skin surface when the array is mounted to such a skin surface) that are electrically connected, via respected matching circuits 515a-e, to an RF switch 520. The RF switch is, in turn, connected via a matching circuit 525 to a transceiver 530.

The RF switch 520 could include a variety of components configured to selectably couple one of the antenna coils 511a-e (via a respective matching circuit 515a-e) to the transceiver 530 via the further matching circuit 525. The RF switch 520 could include one or more transistors, field effect transistors, bipolar transistors, junction field effect transistors, relays, or other electrical switching elements that are controllable to selectably couple one or more terminals of a selected antenna coil (via a corresponding matching circuit) to the transceiver 530 (via the further matching circuit 525). Further, the RF switch 520 could be configured and/or operated to couple non-selected antenna coils to respective specified high or low impedances, e.g., to reduce interference to the operation of the selected antenna coil (e.g., to provide wireless power, to receive wireless transmissions) by the non-selected antenna coils.

The transceiver 530 could include a variety of amplifiers, buffers, oscillators, filters, modulators, or other elements configured to at least one of (i) provide wireless power, via a selected one of the antenna coils 511a-e, to an implanted device or (ii) receive a wireless transmission, via a selected one of the antenna coils 511a-e, from an implanted device. The transceiver 530 could be configured to perform both operations, or to additionally perform further operations, e.g., to transmit wireless transmissions, via a selected one of the antenna coils 511a-e, to an implanted device. In some examples, the transceiver 530 could be configured to provide radio frequency wireless energy, via a selected antenna coil, to an implanted device and to receive a wireless transmission, via the selected antenna coil, as an amount of the provided wireless energy that is backscattered or otherwise reflected by an antenna of the implanted device.

In some examples, an impedance of ports of the RF switch 520 could be substantially different from components, e.g., antenna coils 511a-e, the transceiver 530, to which the RF switch 520 is electrically coupled. In such examples, matching circuits 515a-e, 525 can be provided to match the impedance between components of the reader device 500. Such matching circuits could include coils, chokes, capacitors, striplines, stubs, resistors, or other components configured to transfer radio frequency energy or signals between components of the reader device 500. Such matching circuits could have additional functions, e.g., the matching circuits 515a-e provided between the RF switch 520 and the antenna coils 511a-e could set a resonance frequency, a quality factor, or some other properties of the antenna coils 511a-e. Note that, in some examples, the antenna coil matching circuits 515a-e and/or the further matching circuit 525 could be omitted, e.g., because an impedance of a port of the RF switch 520 substantially matches an impedance of the antenna coils 511a-e and/or the transceiver 530.

Note that the illustrated components of the microelectronic device 400 and external readers 480, 500 are intended as a non-limiting example embodiment and that microelectronic devices and/or external readers as described herein may include more or fewer of the illustrated elements and/or may include further elements. For example, an external reader 480 may not include a light emitter (e.g., 460). In such examples, a target of interest (e.g., a portion of subsurface vasculature) may be illuminated by some other source of light (e.g., ambient light sources). Further examples of implanted devices and external readers configured to power, receive wireless transmissions from, or otherwise interact with such implanted devices are anticipated.

V. EXAMPLE METHODS

Figure 6:
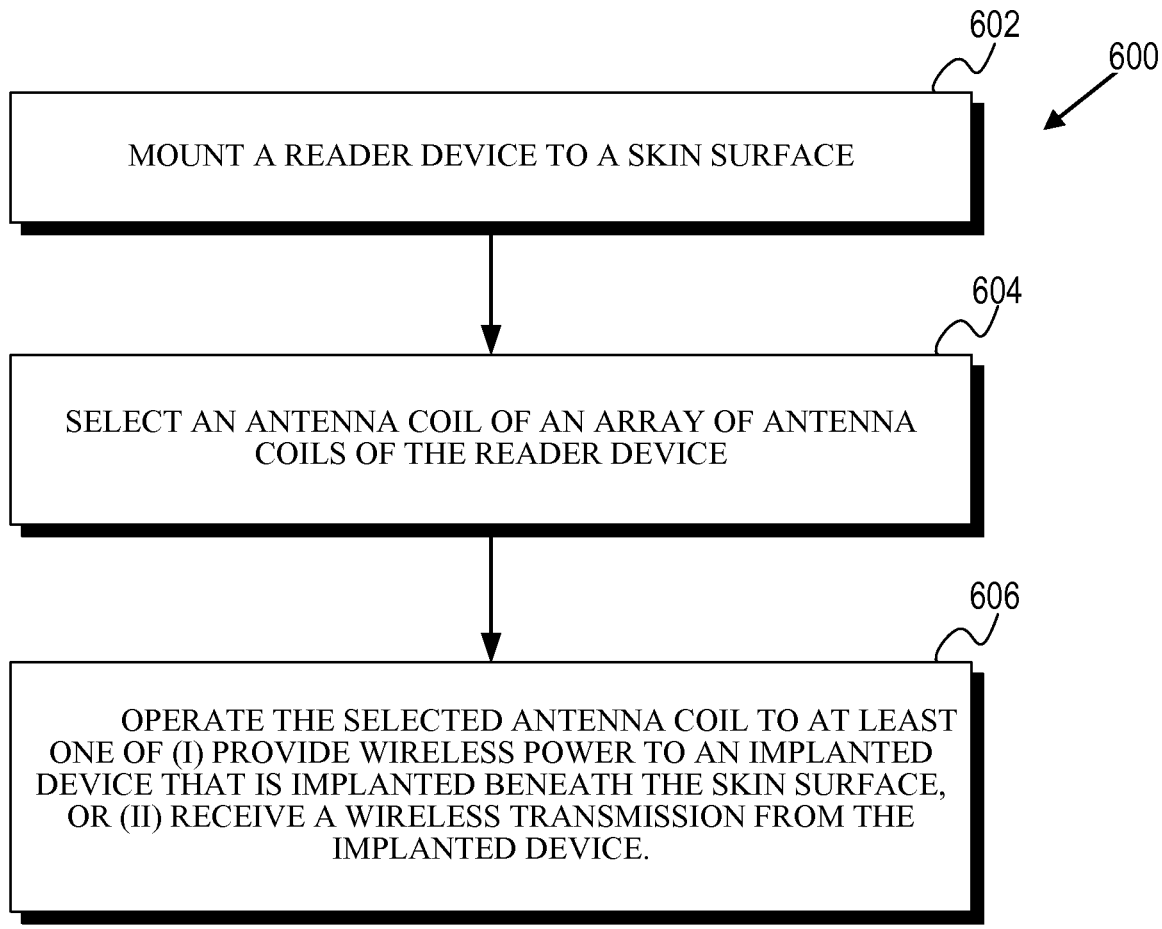
FIG. 6 is a flowchart of an example method for operating a reader device.

FIG. 6 is a flowchart of a method 600 for operating a reader device, e.g., a reader device as described elsewhere herein. The reader device is configured to operate in combination with (e.g., to provide energy to, to receive wireless transmissions from) a microelectronic or otherwise configured device that is implanted in tissue beneath a skin surface. The reader device includes an array of antenna coils the span a specified are of the skin surface. Each antenna coil of the array has a respective degree of electromagnetic coupling with an antenna of the implanted device.

The method 600 includes mounting the reader device to the skin surface 602. This could include placing the reader device proximate the implanted device and maintaining it there by hand. Additionally or alternatively, mounting the reader device to the skin surface could include operating a strap, clasp, adhesive, or other mounting means of the reader device to secure the reader device to a body part, e.g., to a wrist of a wearer in examples wherein the implanted device is located beneath a skin surface of the wrist.

The method 600 further includes selecting an antenna coil of the array of antenna coils 604. Selecting an antenna coil could be performed based on a variety of factors, e.g., based on a degree of coupling between the antenna of the implanted device and each of the antenna coils of the array. This could include determining the location of the implanted device and selecting an antenna coil of the array that is closest to the location of the implanted device. Selecting an antenna coil could include directly or indirectly detecting the degree of electromagnetic coupling between the antenna of the implanted device and each of the antenna coils of the array and selecting the antenna coil having the greatest degree of coupling. For example, selecting an antenna coil could include detecting a received signal strength of a radio frequency signal received (e.g., from the implanted device) by each antenna coil and determining which antenna coil of the array has the greatest received signal strength. In some examples, the radio frequency signal received by a particular antenna coil could be transmitted by the implanted device in response to receiving radio frequency wireless energy from the particular antenna coil; that is, selecting an antenna coil could include using each of the antenna coils of an array to attempt to power, and to receive a responsively transmitted signal from, the implanted device. Selecting an antenna coil 604 could include additional or alternative steps.

The method 600 further includes operating the selected antenna coil to at least one of (i) provide wireless power to the implanted device, of (ii) receive a wireless transmission from the implanted device 606. This could include operating a radio frequency switch to couple the selected antenna coil to a radio frequency receiver, transmitter, and/or transceiver. Operating the selected antenna coil to provide wireless power to the implanted device 606 could include driving the selected antenna coil with radio frequency energy at a specified frequency. In some examples, operating the selected antenna coil 606 could include both of providing wireless power to and receiving a wireless transmission from the implanted device. For example, the selected antenna could be used to provide radio frequency wireless energy to the implanted device, and the implanted device could operate an antenna of the implanted device to control an amount of the provided wireless energy that is backscattered or otherwise reflected to the selected antenna. The selected antenna could then be operated to detect an amplitude, phase, or other properties of the reflected wireless energy to receive a wireless transmission from the implanted device. Operating the selected antenna coil 606 could include further operations, e.g., the selected antenna could be operated to transmit wireless transmissions (e.g., commands, calibration data, operational parameters) to the implanted device.

The method 600 could include additional steps. The method 600 could include transmitting light to the implanted device (e.g., through a portion of subsurface vasculature) such that a light sensor of the implanted device detects a portion of the transmitted light that has been scattered by, reflected by, partially absorbed by, or otherwise transmitted through a target of interest (e.g., the portion of subsurface vasculature). In such examples, a property (e.g., an intensity) of the received light that is detected by the light sensor of the implanted device could be related to a volume of blood in the portion of subsurface vasculature, an oxygen content of such blood, a pressure or flow rate of such blood, or some other hemodynamic or other properties of the target (e.g., a portion of subsurface vasculature and/or blood therein). The method 600 could include determining, by the reader device, such a hemodynamic or other property based on a wireless transmission received from the implanted device (using the selected antenna) that is related to the detected physical variable (e.g., an intensity of received light) detected using the light sensor or some other type of sensor of the implanted device at one or more points in time, e.g., determining a pulse rate, pulse timing, blood pressure, or other properties of a portion of subsurface vasculature and/or blood therein based on received indications of an intensity of light transmitted through the portion of subsurface vasculature and detected using the light sensor at a plurality of different points in time. Emitted light could additionally or alternatively be used to provide optical power to the implanted device, to provide optical wireless transmissions (e.g., commands, programming) to the implanted device, or to provide some other functions. A reader device could include an array of light emitters, and each antenna coil of the reader device could be associated with one or more of the light emitters. Light emitters of such an array could be operated (e.g., to provide illumination, as described above) based on the selection of an antenna coil of the array of antenna coils, i.e., one or more light emitters associated with the selected antenna coil could be operated to provide the illumination. The method 600 could include further steps, or steps alternative to those listed here.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations wherein embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
    an array of antenna coils, wherein the array of antenna coils is configured to be mounted proximate a skin surface and to span a specified area of the skin surface;
    an array of light emitters, wherein the array of light emitters is configured to be mounted proximate the skin surface and to span the specified area of the skin surface when the antenna array is mounted proximate the skin surface, such that light emitted by each light emitter of the array of light emitters illuminates a respective portion of the specified area of the skin surface; and
    a controller operably coupled to the array of antenna coils and to the array of light emitters, wherein the controller comprises a computing device programmed to perform controller operations comprising:
        selecting a particular antenna coil of the array of antenna coils, wherein selecting the particular antenna coil of the array of antenna coils comprises: (a) detecting a received signal strength of a radio frequency signal that is transmitted from an implanted device implanted beneath the skin surface and received by each antenna coil of the array of antenna coils, and (b) determining which antenna coil of the array of antenna coils has the greatest received signal strength;

after selecting the particular antenna coil, operating at least one particular light emitter proximate the particular antenna coil to transmit light to a light sensor of the implanted device through a portion of subsurface vasculature, such that the light sensor detects a property of the subsurface vasculature based on the transmitted light; and operating the particular antenna coil of the array of antenna coils to receive a wireless transmission from the implanted device, wherein the wireless transmission is related to the detected property of the subsurface vasculature.

2. The device of claim 1, wherein at least one antenna coil of the array of antenna coils has a hexagonal shape.

3. The device of claim 1, wherein at least one antenna coil of the array of antenna coils has a diameter between 3 millimeters and 3.5 millimeters.

4. The device of claim 1, wherein the windings of individual antenna coils of the array of antenna coils are separated from each other by at least 0.5 millimeters.

5. The device of claim 1, wherein the device further comprises a ground plane that is separated from the array of antenna coils by a spacing layer.

6. The device of claim 1, further comprising a contact layer, wherein the contact layer is configured to be in contact with the skin surface and to be disposed between the skin surface and the array of antenna coils when the array of antenna coils is mounted proximate the skin surface.

7. The device of claim 6, wherein the contact layer has a relative permittivity that is less than 3.5 and a loss tangent that is less than 0.002.

8. The device of claim 6, wherein the contact layer has a thickness that is between 0.1 millimeters and 0.4 millimeters.

9. The device of claim 1, wherein the device comprises a window through the array of antenna coils, and wherein at least one light emitter of the array of light emitters is configured to illuminate a portion of the skin surface though the window.

10. The device of claim 1, further comprising:
a radio frequency switch, wherein each antenna coil of the array of antenna coils is coupled to the radio frequency switch, wherein the controller is operably coupled to the radio frequency switch, and wherein operating the particular antenna coil of the array of antenna coils comprises operating the radio frequency switch to couple the particular antenna coil to the controller.

11. The device of claim 10, wherein each antenna coil of the array of antenna coils is coupled to the radio frequency switch via a respective matching circuit.

12. The device of claim 1, wherein the at least one particular light emitter includes a light emitter disposed at a center of the particular antenna coil.

13. The device of claim 1, wherein the at least one particular light emitter includes a light emitter that is offset from a center of the particular antenna coil.

14. A method comprising:
mounting a reader device to a skin surface, wherein the reader device comprises an array of antenna coils that spans a specified area of the skin surface and an array of light emitters that spans the specified area of the skin surface, wherein an implanted device is implanted beneath the skin surface;

selecting a particular antenna coil of the array of antenna coils, wherein selecting the particular antenna coil of the array of antenna coils comprises: (a) detecting a received signal strength of a radio frequency signal that is transmitted from an implanted device implanted beneath the skin surface and received by each antenna coil of the array of antenna coils, and (b) determining which antenna coil of the array of antenna coils has the greatest received signal strength;

after selecting the particular antenna coil, operating at least one particular light emitter proximate the particular antenna coil to transmit light to a light sensor of the implanted device through a portion of subsurface vasculature, such that the light sensor detects a property of the subsurface vasculature based on the transmitted light; and operating the particular antenna coil of the array of antenna coils to receive a wireless transmission from the implanted device, wherein the wireless transmission is related to the detected property of the subsurface vasculature.

15. The method of claim 14, wherein at least one antenna coil of the array of antenna coils has a diameter between 3 millimeters and 3.5 millimeters.

16. The method of claim 14, wherein the reader device further comprises a contact layer, wherein the contact layer is configured to be in contact with the skin surface and to be disposed between the skin surface and the array of antenna coils when the array of antenna coils is mounted proximate the skin surface, and wherein the contact layer has a thickness that is between 0.1 millimeters and 0.4 millimeters.

17. The method of claim 14, wherein the radio frequency signal received by a given antenna coil is transmitted by the implanted device responsive to radio frequency energy transmitted by the given antenna coil.

18. The method of claim 14, wherein the at least one particular light emitter includes a light emitter disposed at a center of the particular antenna coil.

19. The method of claim 14, wherein the at least one particular light emitter includes a light emitter that is offset from a center of the particular antenna coil.

* * * * *